US008044048B2

(12) United States Patent
Piazza et al.

(10) Patent No.: US 8,044,048 B2
(45) Date of Patent: Oct. 25, 2011

(54) DERIVATIVES OF SULINDAC, USE THEREOF AND PREPARATION THEREOF

(75) Inventors: Gary Piazza, Vestavia, AL (US); Robert Reynolds, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 1164 days.

(21) Appl. No.: 11/649,373

(22) Filed: Jan. 4, 2007

(65) Prior Publication Data
US 2007/0244122 A1 Oct. 18, 2007

Related U.S. Application Data

(60) Provisional application No. 60/755,847, filed on Jan. 4, 2006.

(51) Int. Cl.
C07C 233/04 (2006.01)
C07D 207/08 (2006.01)
C07D 233/64 (2006.01)
C07D 213/36 (2006.01)
C07D 295/10 (2006.01)
C07D 241/04 (2006.01)
A61K 31/40 (2006.01)
A61K 31/4453 (2006.01)
A61K 31/44 (2006.01)
A61K 31/495 (2006.01)
A61K 31/5375 (2006.01)
A61K 31/341 (2006.01)
A61K 31/4164 (2006.01)
A61K 31/16 (2006.01)

(52) U.S. Cl. ............ 514/238.8; 514/618; 514/428; 514/252.12; 514/319; 514/277; 544/399; 544/161; 546/205; 546/340; 548/571; 564/162

(58) Field of Classification Search .................. None
See application file for complete search history.

(56) References Cited

U.S. PATENT DOCUMENTS

| 3,161,654 | A |   | 12/1964 | Shen et al. |
|---|---|---|---|---|
| 3,647,858 | A |   | 3/1972 | Hinkley et al. |
| 3,654,349 | A |   | 4/1972 | Shen et al. |
| 3,851,063 | A |   | 11/1974 | Shen et al. |
| 4,423,075 | A |   | 12/1983 | Dvornik et al. |
| 5,401,774 | A |   | 3/1995 | Pamukcu et al. |
| 5,475,021 | A |   | 12/1995 | Marnett et al. |
| 5,643,959 | A |   | 7/1997 | Pamukcu et al. |
| 5,858,694 | A |   | 1/1999 | Piazza et al. |
| 5,942,520 | A |   | 8/1999 | Pamukcu et al. |
| 5,973,191 | A |   | 10/1999 | Marnett et al. |
| 6,063,818 | A |   | 5/2000 | Sperl et al. |
| 6,071,934 | A | * | 6/2000 | Sperl et al. ............ 514/332 |
| 6,130,053 | A | * | 10/2000 | Thompson et al. ......... 435/15 |
| 6,166,053 | A |   | 12/2000 | Sperl et al. |
| 6,200,771 | B1 |   | 3/2001 | Liu et al. |
| 6,403,831 | B1 |   | 6/2002 | Sperl et al. |

| 2001/0034361 | A1 | 10/2001 | Kalgutkar et al. |
|---|---|---|---|
| 2004/0192929 | A1 | 9/2004 | Allegrini et al. |
| 2005/0090553 | A1 | 4/2005 | Shapiro |
| 2005/0250839 | A1 | 11/2005 | Marnett et al. |

FOREIGN PATENT DOCUMENTS

| CA |   | 958032 A2 | * | 11/1974 |
|---|---|---|---|---|
| EP |   | 0881300 B1 |   | 1/2001 |
| WO |   | WO-9821195 |   | 5/1998 |
| WO |   | WO 0011022 A1 | * | 3/2000 |
| WO |   | WO 0027194 A1 | * | 5/2000 |

OTHER PUBLICATIONS

Kalgutkar et al., Biochemically Based Design of Cyclooxygenase-2 (COX-2) Inhibitors: Facile Conversion of Nonsteroidal Antiinflammatory Drugs to Potent and Highly Selective COX-2 Inhibitors, PNAS, Jan. 18, 2000, vol. 97, No. 2, 925-930.
Kalgutkar et al., Ester and Amide Derivatives of the Nonsteroidal Antiinflammtory Drug, Indomethacin, As Selective Cyclooxygenase-2 Inhibitors, J. Med. Chem, 2000, vol. 43, No. 15, 2860-2870.
Kalgutkar et al., Amide Derivatives of Meclofenamic Acid as Selective Cyclooxygenase-2 Inhibitors, Bioorg. Med. Chem. Lett. 12 (2002) 521-524.
English language translation of Office Action dated Apr. 2, 2010 from corresponding Eurasian Application No. 200870148/(OFE/0808/0005).
Office Action dated Mar. 16, 2010 from corresponding Canadian Application No. 2,635,093.
Documents filed May 26, 2010 with EPO in corresponding European Application No. 07716225.3-2112.
English language translation of Office Action dated Mar. 23, 2010 from corresponding Chinese Application No. 200780001936.4.
Communication dated Nov. 24, 2009 and Supplementary European Search Report dated Oct. 6, 2009 in corresponding European Application No. 07716225.3-2112.
Examination Report dated Mar. 10, 2010 from corresponding New Zealand Application No. 569370.
Bennett et al., Increased Survival of Cancer-Bearing Mice Treated With Inhibitors of Prostaglandin Synthesis Alone or With Chemotherapy, Br. J. Cancer (1982) 45, 762.
Timothy A. Chan, Nonsteroidal Anti-Inflammatory Drugs, Apoptosis, and Colon-Cancer Chemoprevention, The Lancet Oncology, vol. 3, Mar. 2002, 166-174.
Chau et al., Cyclooxygenase Inhibition In Cancer—A Blind Alley or a New Therapeutic Reality?, N. Engl. J. Med., vol. 346, No. 14, Apr. 4, 2002, 1085-1087.
DuBois et al., Editorials, Journal of the National Cancer Institute, vol. 94, No. 23, Dec. 4, 2002.
Duggan et al., The Disposition of Sulindac, Clinical Pharmacology and Therapeutics, vol. 21, No. 3, Nov. 4, 1976, 326-335, (1979).

(Continued)

Primary Examiner — Yong Chu
Assistant Examiner — Michael Barker
(74) Attorney, Agent, or Firm — Connolly Bove Lodge & Hutz LLP

(57) ABSTRACT

Derivatives of sulindac are provided along with pharmaceutical compositions containing them and use for precancerous conditions and treating cancer. Derivatives of sulindac are also suitable for treating chronic inflammatory conditions. A method for preparing the derivatives is also provided.

33 Claims, 6 Drawing Sheets

OTHER PUBLICATIONS

Duggan et al., Kinetics of the Tissue Distributiions of Sulindac and Metabolites, Drug and Metabolism and Dispositions, Sulindac Pharmacokinetics, vol. 8, No. 4, pp. 241-246.

Duggan et al., Identification of the Biologically Active Form of Sulindac, The Journal of Pharmacology and Experimental Therapeutics, vol. 201, No. 1, 1977, pp. 8-13.

Duggan et al., Comparative Disposition of Sulindac and Metabolites in Five Species, Biological Pharmacology, vol. 27, pp. 2311-2320, (1978).

Ervin Y. Eaker, Gastrointestinal Injury Related to use of Nonsteroidal Anti-Inflammatory Drugs, Gatrointestinal Diseases Today, vol. 6, No. 6, 1977, pp. 1-8.

Elliott et al., A Nitric Oxide-Releasing Nonsteroidal Anti-Inflammatory Drug Accelerates Gastric Ulcer Healing in Rate, Gastroenterology 1995, vol. 109, pp. 524-530.

Amy M. Fulton, Inhibition of Experimental Metastasis With Indomethacin: Role of Macrophages and Natural Killer Cells, Prostaglandins, Mar. 1988 vol. 35 No. 3, pp. 413-425.

Giardiello et al., Treatment of Colonic and Rectal Adenomas with Sulindac in Familial Adenomatous Polyposis, New England Journal of Medicine, vol. 328, 1993, No. 18, pp. 1313-1316.

Hial et al., Alternation of Tumor Growth by Aspirin and Indomethacin: Studies with Two Transplantable Tumors in Mouse, European Journal of Pharmacology, 37 (1976) 367-376.

Janne et al., Chemoprevention of Colorectal Cancer, New England Journal of Medicine, 2000, vol. 342, No. 26, 1960-1968.

Karaguni et al., New Indene-Derivatives with Anti-Proliferative Properties, Bioorganic & Medicinal Chemistry Letters, 12 (2002) 709-713.

Karaguni et al., The New Sulindac Derivative IND 12 Reverses Ras-induced Cell Transformation, Cancer Research 62, 1718-1723, Mar. 15, 2002.

Labayle et al., Sulindac Causes Regression of Rectal Polyps in Familial Adenomatous Polyposis, Gastroenterology, 1991, vol. 101, pp. 635-639.

Llorens e tal., Differential Binding Mode of Diverse Cyclooxygenase Inhibitors, Journal of Molecular Graphics and Modelling, 20 (2002), pp. 359-371.

Lynch et al., Mechanism of Inhibition of Tumour Growth By Aspirin and Indomethacin, Br. J. Cancer, (1978) 38, 503.

Mahmud et al., A Unifying Hypothesis for the Mechanism of NSAID Related Gastrointestinal Toxicity, Annals of the Rheumatic Diseases, 1996, vol. 55, pp. 211-213.

Moorghen et al., A Protective Effect of Sulindac Against Chemically-Induced Primary Colonic Tumors in Mice, Journal of Pathology, vol. 156, 341-347 (1988).

Moorghen et al., The Effect of Sulindac on Colonic Tumor Formation in Dimethylhydrazine-treated Mice, Acta histochemica, Suppl.-Band XXXIX, S. 195-199 (1990).

Mukherjee et al., Risk of Cardiovascular Events Associated With Selective COX-2 Inhibitors, JAMA, 2001, vol. 286, pp. 954-959.

Myers et al., Proapoptotic Anti-Inflammatory Drugs, Urology, 57 (Supplemental 4A), Apr. 2001, pp. 73-76.

Nugent et al., Randomized Controlled Trial of the Effect of Sulindac on Duodenal and Rectal Polyposis and Cell Proliferation in Patients with Familial Adenomatous Polyposis, Br. J. Surg., 1993, vol. 80, December, pp. 1618-1619.

Biff Palmer, Renal Complications Associated with Use of Nonsteroidal Anti-Inflammatory Agents, Journal of Investigative Medicine, vol. 43, No. 6, Dec. 1995, pp. 516-533.

Piazza et al., Apoptosis Primarily Accounts for the Growth-Inhibitory Properties of Sulindac Metabolites and Involves a Mechanism That Is Independent of Cyclooxygenase Inhibition, Cell Cycle Arrest, and p53 Induction, Cancer Research, 57, 2452-2459, Jun. 15, 1997.

Piazza et al., Sulindac Sulfone Inhibits Azoxymethane-induced Colon Carcinogenesis in Rats Without Reducing Prostaglandin Levels, Cancer Research, 57, 2909-2915, Jul. 15, 1997.

Piazza et al., Exisulind, A Novel Proapoptotic Drug, Inhibits Rat Urinary Bladder Tumorigenesis, Cancer Research, 61, 3961-3968, May 15, 2001.

Piazza et al., Antineoplastic Drugs Sulindac Sulfide and Sulfone Inhibit Cell Growth by Inducing Apoptosis, Cancer Research, 55, 3110-3116, Jul. 15, 1995.

Pollard et al., Prolonged Antitumor Effect of Indomethacin on Autochthonous Intestinal Tumors in Rats, JNCI, vol. 70, No. 6, Jun. 1983.

Shen et al., Chemical and Biological Studies on Indomethacin, Sulindac and Their Analogs, pp. 89-245, (1977).

Strong et al., Sulindac Metabolism: The Importance of An Intact Colon, Clin. Pharm. Th. vol. 38, No. 4, Oct. 1983, pp. 387-393.

Strul et al., Non-Steroidal Anti-Inflammatory Drugs and Selective Apoptotic Anti-Neoplastic Drugs in the Prevention of Colorectal Cancer: The Role of Super Aspirins, IMAJ, vol. 2, Sep. 2000, pp. 695-702.

Swanson et al., Sulindac Disposition When Given Once and Twice Daily, Clin. Pharmacol. Ther., vol. 12, No. 3, Sep. 1982. pp. 397-403.

Tarazi et al., Sulindac-Associated Hepatic Injury: Analysis of 91 Cases Reported to the Food and Drug Administration, Gastroenterology, vol. 104, No. 2, 1993, pp. 569-574.

Thompson et al., Exisulind Induction of Apoptosis Involves Guanosine 3',5'-Cyclic Monophosphate Phosphodiesterase Inhibition, Protein Kinase G Activation, and Attenuated β-Catenin, Cancer Research, 60, 3338-3342, Jul. 1, 2000.

Thun et al., Experts Scout Aspirins's Anticancer Promise, The Journal of NIH Research, Mar. 1992, vol. 4, pp. 70-75.

J.R. Vane, Mode of Action of Aspirin and Similar Compounds, The Wellcome Research Laboratories, Beckenham, Kent, England, 1974, pp. 155-163.

Venuti et al., Synthesis and Biological Evaluation of Ω-($N,N,N$-Trialkylammonium)alkyl Esters and Thioesters of Carboxylic Acid Nonsteroidal Antiinflammatory Agents, Pharmaceutical Research, vol. 6, No. 10, 1989, pp. 867-873.

Waddell et al., Sulindac for Polyposis of the Colon, The Amernical Journal of Surgery, vol. 157, Jan. 1989, pp. 175-179.

Waldmann et al., Sulindac-Derived Ras Pathway Inhibitors Target the Ras-Raf interaction and downstream Effectors in the Ras Pathway, Angew. Chem. Int. Ed. 2004, 43, 454-458.

Gerald Weissmann, Aspirin, Scientific American, Jan. 1991, pp. 84-90.

Winde et al., Complete Reversion and Prevention of Rectal Adenomas in Colectomized Patients with Familial Adenomatous Polyposis by Rectal Low-Dose Sulindac Maintenance Treatment, Dis. Colon Rectum, vol. 38, No. 8, Aug. 1995, pp. 813-830.

Wolfe et al., Gastrointestinal Toxicity of Nonsteroidal Antiinflammatory Drugs, The New England Journal of Medicine, vol. 340, No. 24, Jun. 17, 1999, pp. 1888-1899.

Salimbeni et al., New Esters of N-Arylanthranilic Acids, e Coll., II Farmaco—Ed. Sc.—vol. 30, fasc. 4, pp. 276-286, (1976).

Waddell et al., Sulindac for Polyposis of the Colon, Journal of Surgical Oncology, 24:83-87 (1983).

Smith et al., March's Advanced Organic Chemistry—Reactions, Mechanisms and Structure, Fifth Edition, Chapter 10, Aliphatic Nucleophilic Substitution, pp. 506-512, (2001).

Federation Proceedings (1972) of the Federation of Amernican Societies for Experimental Biology Abstract Nos. 2044 and 2045.

Gonzaga et al., Sulindac Treatment for *Familial Polyposis Coli*, The Lancet, Mar. 30, 1985, p. 751.

Gilman et al., Nonsteroidal Anti-Inflammatory Drugs in Cancer Therapy (CIRCA 1985) pp. 157-179.

Hucker et al. Physiologic Disposition and Metabolic Fate of a New Anti-Inflammatory Agent, cis-5-Fluoro-2-Methyl-1-[p-(Methylsulfinyl)-Benzylidenyl]-Indene-3-Acetic Acid in the Rat, Dog Rhesus Monkey, and Man, Drug Metabolism & Disposition, vol. 1, No. 6, pp. 721-736 (1973).

Bjarnason et al., Clinicopathological Features of Nonsteroidal Antiinflammatory Drug-Induced Small Intestinal Strictures, Gastroenterology, vol. 94, No. 4, pp. 1070-1074 (1988).

Glavin et al., Short Communication—The Effects of Sulindac and Its Metabolites on Acute Stress-Induced Gastric Ulcers in Rats, Toxicology and Applied Pharmacology, vol. 83, pp. 386-389 (1986).

Instructor Patrick M. Woster, PHA 413—Immunology, Inflammatory Diseases and Hematology Medicinal Chemistry Tutorial, Ph.D.: dated Jan. 20, 2003.

* cited by examiner

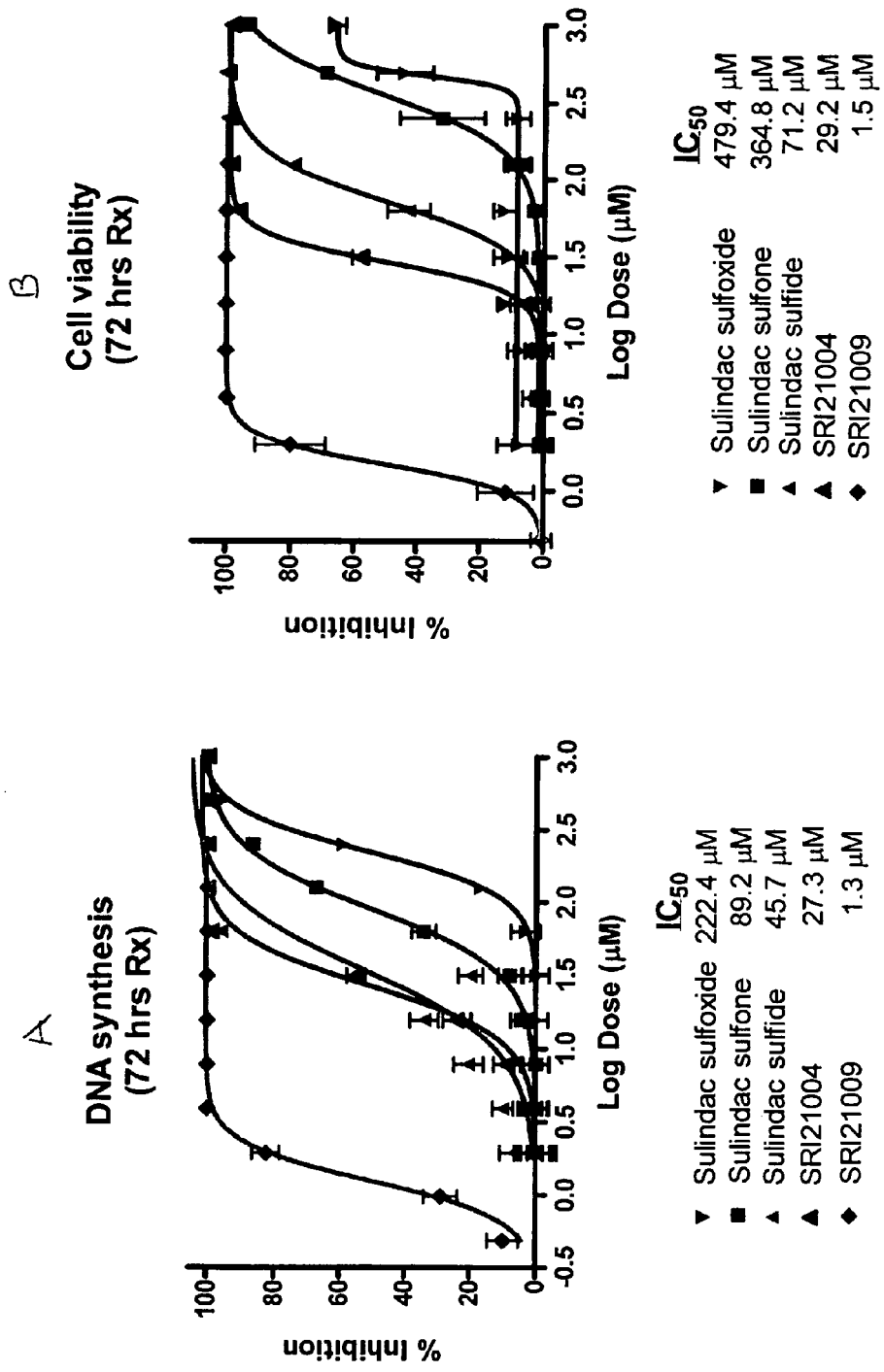
Figure 1. Growth inhibitory activity of SRI derivatives and sulindac against human HT29 colon cells

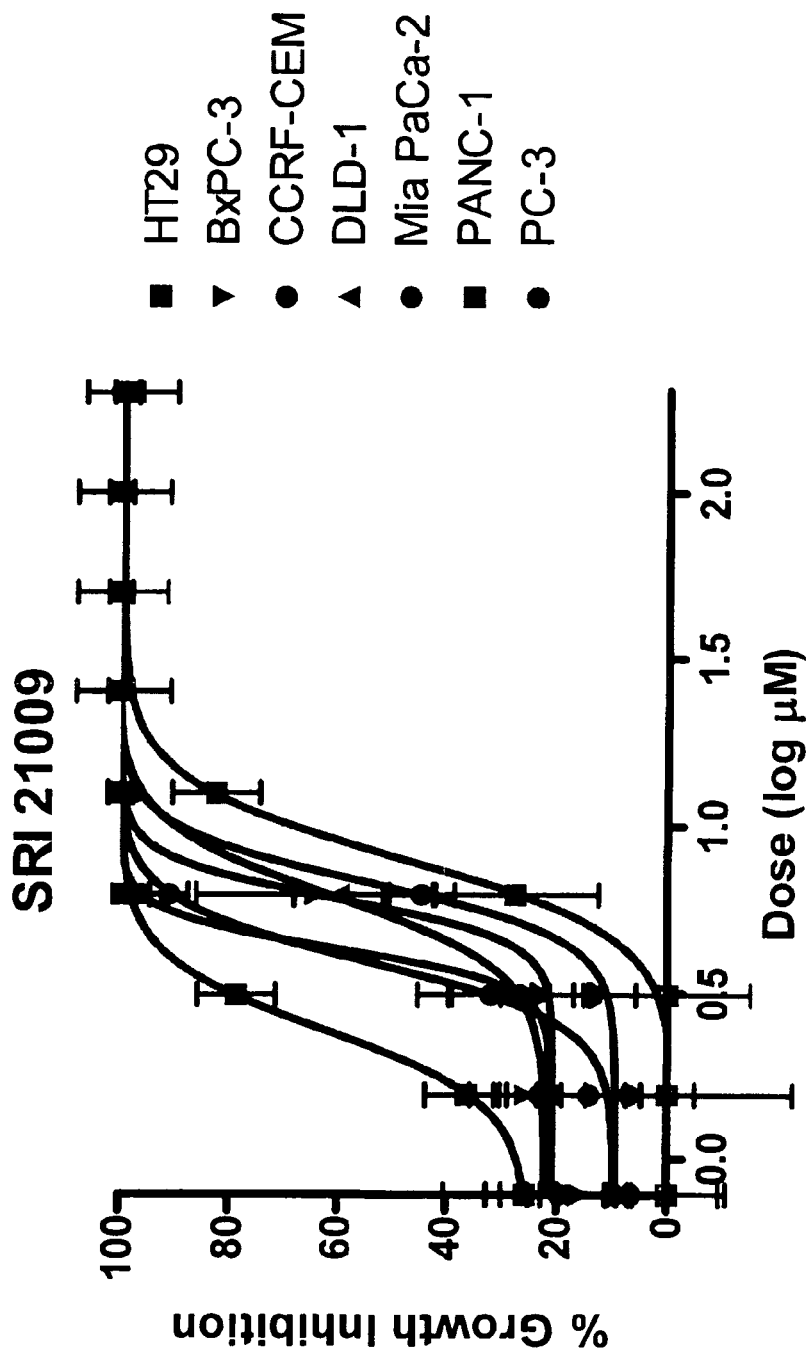
Figure 2. Growth inhibitory activity of SRI 21009 against a panel of human tumor lines

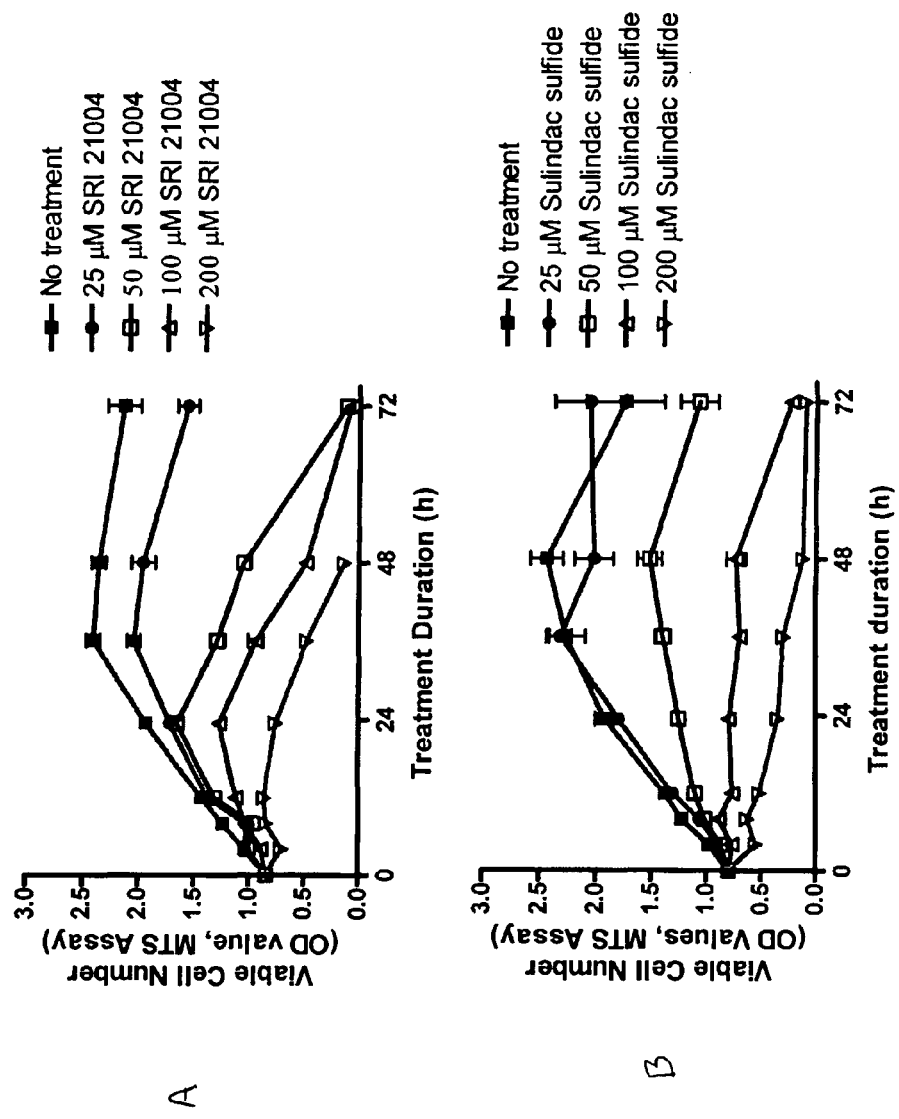
Figure 3. Cytostatic and cytotoxic effects of SRI 21004 and sulindac sulfide against human HT29 colon tumor cell growth

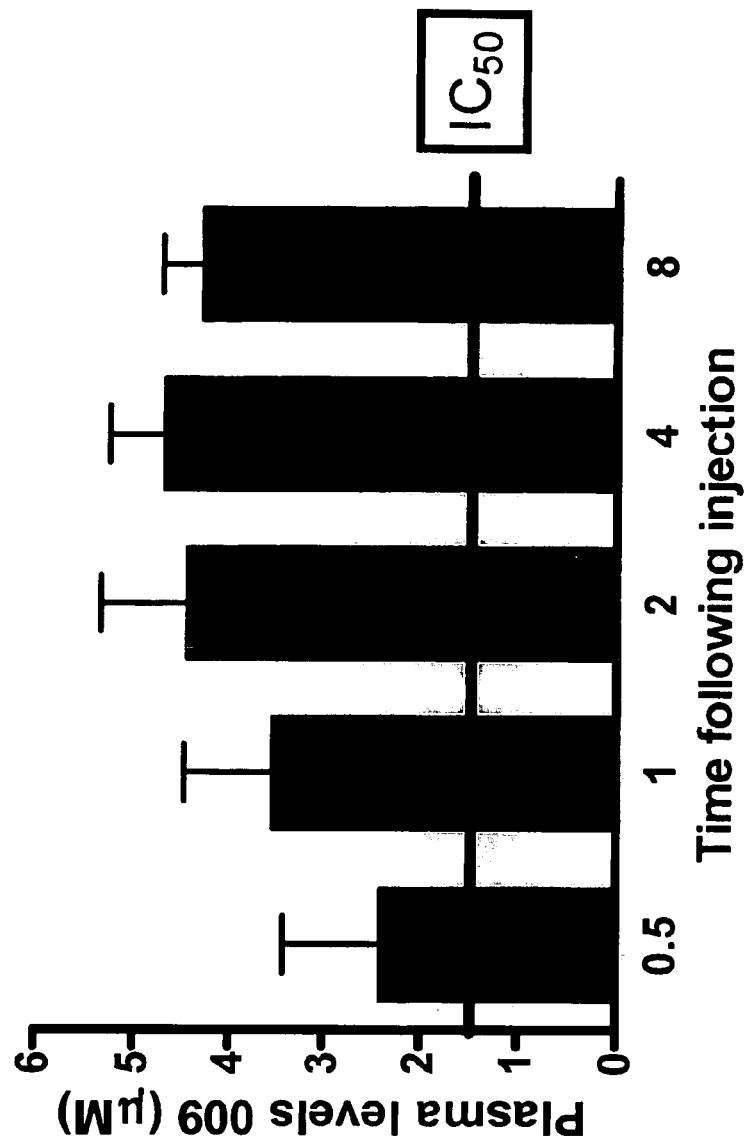
Figure 4. SRI 21009 Pharmacokinetics

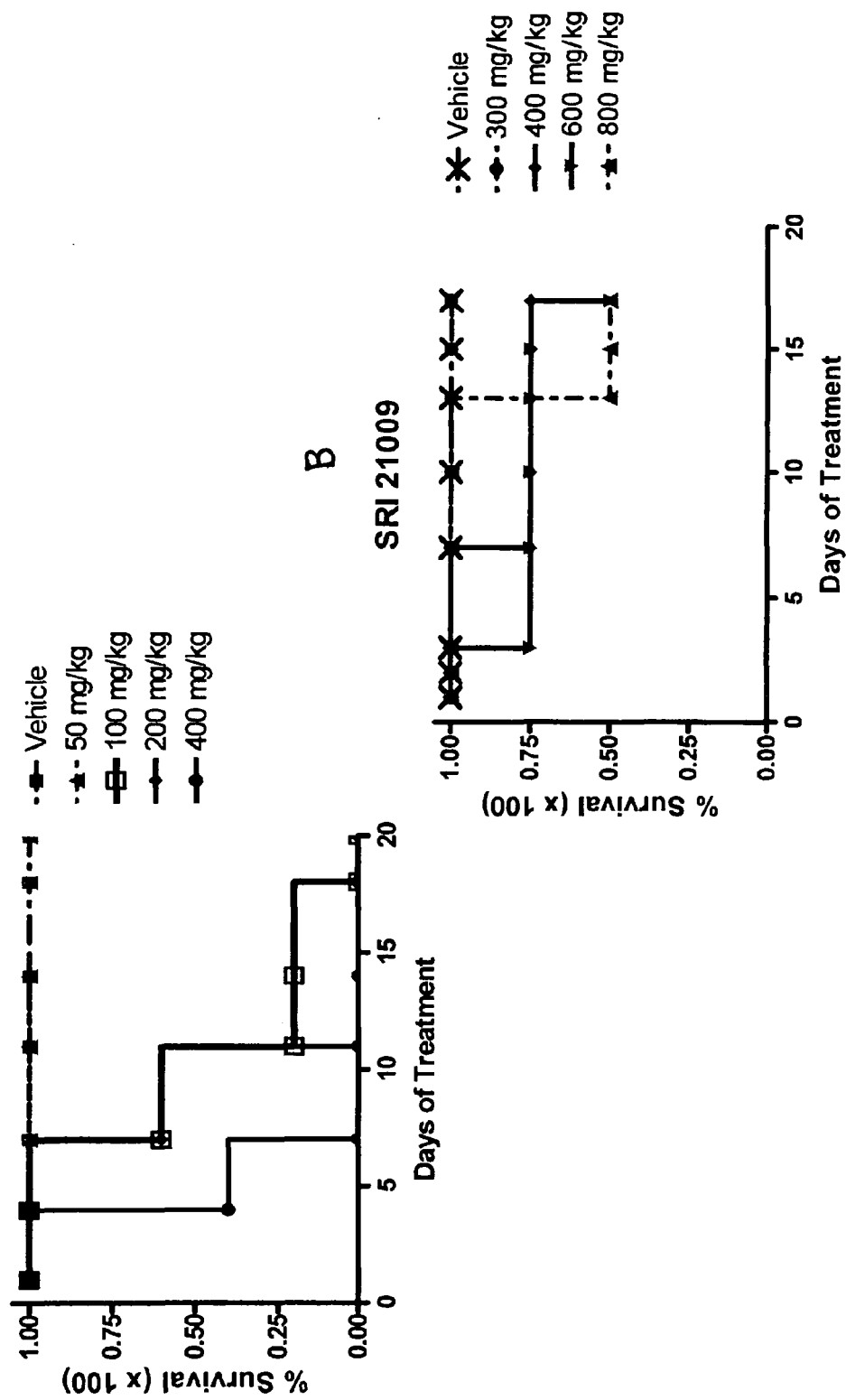
Figure 5. Toxicity comparison of sulindac and SRI 21009 in mice

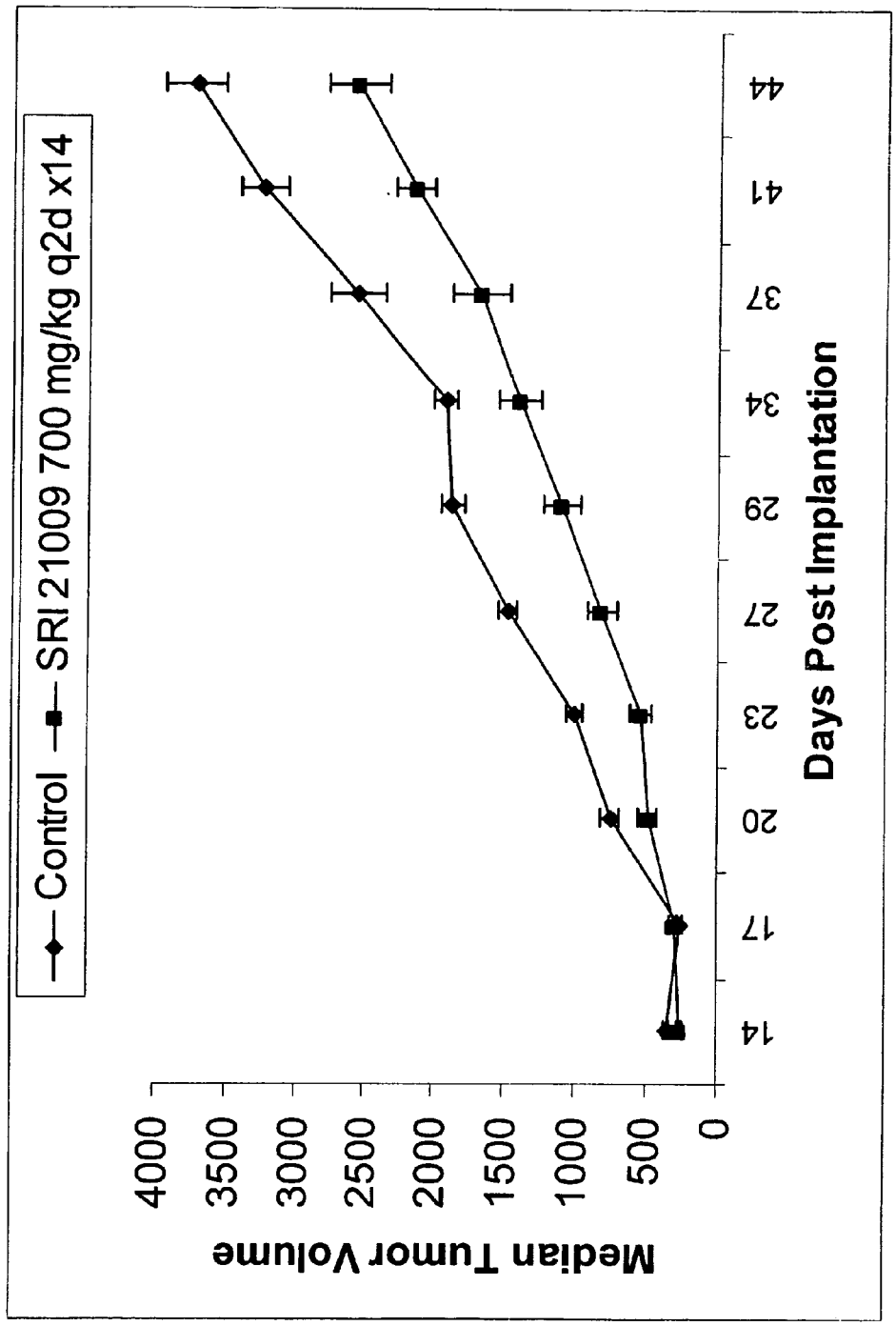
Figure 6. *In vivo* growth inhibitory activity of SRI 21009 vs. human HT29 colon tumor xenografts in athymic nude mice

DERIVATIVES OF SULINDAC, USE THEREOF AND PREPARATION THEREOF

CROSS-REFERENCE TO RELATED APPLICATIONS

This application claims priority from U.S. Ser. No. 60/755,847, filed on Jan. 4, 2006, entire disclosure of which is incorporated herein by reference

TECHNICAL FIELD

The present disclosure relates to certain derivatives of sulindac and especially to amide derivatives of sulindac. The present disclosure also relates to pharmaceutical compositions comprising the disclosed derivatives of sulindac, as well as a method of using the compounds in the treatment and prevention of precancerous conditions and cancer in a mammal. The present disclosure also relates to a method for producing the disclosed compounds.

BACKGROUND

Even though significant advances have occurred in the treatment of cancer, it still remains a major health concern. Cancer has been reported as the leading cause of death in the United States with one of every four Americans likely to be diagnosed with the disease.

Included among the known chemotherapeutic drugs are carmustine, doxorubicin, methotrexate, paclitaxel, cyclophosphamide, procarbazine, and vinblastine, to name only a few. However, many chemotherapeutic drugs also produce undesirable side effects in the patient.

Certain nonsteroidal anti-inflammatory drugs (NSAIDs) have been recognized to have broad anticancer activity in animal models alone and in combination with chemotherapy or radiation. Representative examples include: Hial et al., "Alteration of tumor growth by aspirin and indomethacin: studies with two transplantable tumors in mouse" Eur. J. Pharm. 37: 367-376, 1976; Lynch et al., "Mechanism of inhibition of tumor growth by aspiring and indomethacin" Br. J. Cancer 38: 503-512, 1978; Bennett et al., "Increased survival of cancer-bearing mice treated with inhibitors of prostaglandin synthesis alone or with chemotherapy" Br. J. Cancer 45: 762-768, 1982; Pollard and Luckert "Prolonged antitumor effect of indomethacin on autochthonous intestinal tumors in rats" J. Natl. Cancer Inst. 70: 1103-1105, 1983; Fulton, "Inhibition of experimental metastasis with indomethacin: role of macrophages and natural killer cells" Prostaglandins: 35: 413-425, 1988; Moorghen et al., "The effect of sulindac on colonic tumor formation in dimethylhydrazine-treated mice" Acta histochemica 29: 195-199, 1990; and Moorghen et al., "A protective effect of sulindac against chemically-induced primary colonic tumours in mice" J. of Path. 156: 341-347.

Sulindac (Clinoril™) is a NSAID that has demonstrated anticancer activity. It has been recognized as having benefits for treating dysplasia as evidenced by a number of clinical trials in familial adenomatous polyposis patients which have shown the ability of sulindac to cause the regression of existing adenomas (size and number) and inhibit new adenoma (polyp) formation. For example, see Waddell et al, "Sulindac for polyposis of the colon". J. of Surg. 157: 175-179, 1989; Labayle et al., "Sulindac causes regression of rectal polyps in familial adenomatous polyposis" Gastroenterology 101: 635-639, 1991; Nugent et al., "Randomized controlled trial of the effect of sulindac on duodenal and rectal polyposis and cell proliferation in patients with familial adenomatous polyposis" Br. J. Surg. 80: 1618-1619, 1993; Giardiello, et al., "Treatment of colonic and rectal adenomas with sulindac in familial adenomatous polyposis" N. Eng. J. Med 328: 1313-6, 1993; and Winde et al., "Complete reversion and prevention of rectal adenomas in colectomized patients with familial adenomatous polyposis by rectal low-dose sulindac maintenance treatment." Dis. Colon Rectum 38: 813-830, 1995.

The mechanism responsible for the anti-inflammatory efficacy and as well as the toxicity of NSAIDs and COX-2 selective inhibitors (gastrointestinal, renal, hematological, cardiovascular) has been shown to involve cyclooxygenase (COX)-1 or COX-2 inhibition. Sulindac and certain other NSAIDs also have hepatic toxicity. For instance, see Vane, "Mode of action of aspirin and similar compounds" In Prostaglandin Synthetase Inhibitors, Eds Robinson, Raven Press, New York, N.Y., 1974; Eaker "Gastrointestinal injury related to the use of nonsteroidal anti-inflammatory drugs" Gastrointestinal Disease Today 6: 1-8, 1997; Wolfe et al., "Gastrointestinal toxicity of nonsteroidal anti-inflammatory drugs" N. Eng. J. Med 340: 1888-99, 1999; Palmer "Renal complications associated with use of nonsterdoidal anti-inflammatory agents" J. Invest. Medicine 43: 516-533, 1995; Tarazi et al., "Sulindac-associated hepatic injury: analysis of 91 cases reported to the Food and Drug Administration" Gastroenterology 104: 569-574, 1993; and Mukherjee et al. "Risk of cardiovascular events associated with selective COX-2 inhibitors" JAMA 286: 954-959, 2001.

Most investigators attribute the mechanism for the anticancer activity of NSAIDs to anti-inflammatory activity involving COX inhibition, although there is evidence for a COX-independent mechanism as mentioned below. For example, the activity of the sulfone metabolite of sulindac has been described which retains anticancer activity in preclinical and clinical trials but does not inhibit cyclooxygenase and displays less GI toxicity. See for example, Piazza et al., "Antineoplastic drugs sulindac sulfide and sulfone inhibit cell growth by inducing apoptosis" Cancer Res. 55: 3110-3116, 1995; Piazza et al., "Sulindac sulfone inhibits azoxymethane-induced colon carcinogenesis in rats without reducing prostaglandin levels" Cancer Res. 57: 2909-2915, 1997; Piazza et al., "Apoptosis primarily accounts for the growth inhibitory properties of sulindac metabolites and involves a mechanism that is independent of cyclooxygenase inhibition, cell cycle arrest, and p53 induction" Cancer Res. 57: 2452-2459, 1997; Piazza et al, "Exisulind a novel proapoptotic drug inhibits rat urinary bladder tumorigenesis" Cancer Res., 61: 3961-3968, 2001; and Chan "Nonsteroidal anti-inflammatory drugs, apoptosis, and colon-cancer chemoprevention" The Lancet Oncology 3: 166-174, 2002.

There are publications suggesting that certain chemical modifications to the carboxylic acid moiety of NSAIDs will result in improved safety (i.e., as prodrugs or by localized release of nitric oxide). For example, see Mahmud et al., "A unifying hypothesis for the mechanism of NSAID related gastrointestinal toxicity". Ann. Rheumatic Diseases 55: 211-213, 1996; Venuti et al., "Synthesis and biological evaluation of (N,N,N,-trialkylammonium) alkyl esters and thioesters of carboxylic acid nonsteroidal anti-inflammatory drugs" Pharmaceutical Research 6: 867-873, 1989; Salimbeni et al., "New esters of N-arylanthranilic acids" Farmaco 30: 276-86, 1975; and Elliot et al. "A nitric oxide-releasing nonsteroidal anti-inflammatory drug accelerates gastric ulcer healing in rats" Gastroenterology 109: 524-530, 1995.

In addition, U.S. Pat. Nos. 5,401,774, 6,166,053 and 6,200,771 suggest certain modifications to sulindac sulfone which is not a NSAID.

A series of amide and ester derivatives of indomethacin and meclofenamic acid involving modifications to the carboxylic acid moiety were described by Marnett et al. These compounds were described as having safety advantages over the parent NSAIDs based on selectivity for the cyclooxygenase-2 isozyme. However, anticancer activity was not described and modifications to improve anticancer efficacy (potency) were not described. For example, see Kalgutkar et al., "Biochemical based design of cyclooxygenase-2 (COX-2) inhibitors: facile conversion of nonsteroidal anti-inflammatory drugs to potent and highly selective COX-2 inhibitors" Proc. Natl. Acad. Sci. 97: 925-930, 2000; Kalgutkar et al. "Amide derivatives of meclofenamic acid as selective cyclooxygenase-2 inhibitors" Bioorganic and Medicinal Chemistry Letters 12: 521-524, 2002; Kalgutkar et al., "Ester and amide derivatives of the nonsteroidal anti-inflammatory drug, indomethacin, as selective cyclooxygenase-2 inhibitors" J. Med. Chem. 43: 2860-2870, 2000; U.S. Pat. No. 5,973,191 to Marnett and Kalgutkar "Selective inhibitors of prostaglandin endoperoxide synthetase-2"; and U.S. Pat. No. 5,475,021 to Marnett and Kalgutkar "Compounds and compositions for inhibition of cyclooxygenase activity".

It cannot be predicted that chemical modifications to one family of NSAIDs are applicable to another family. For instance, meclofenamic acid belongs to the fenamate family, while sulindac belongs to the acetic acid family of NSAIDs and therefore are not structurally similar to each other. Additionally, not all amide modifications to the carboxylic acid result in increased COX-2 selectivity as demonstrated in this disclosure.

Notwithstanding the advances in treatments for cancer and other diseases there still remains room for improved drugs that are effective for the desired treatment, while at the same time exhibiting reduced adverse side effects.

SUMMARY

The present disclosure relates to derivatives of sulindac represented by the formula:

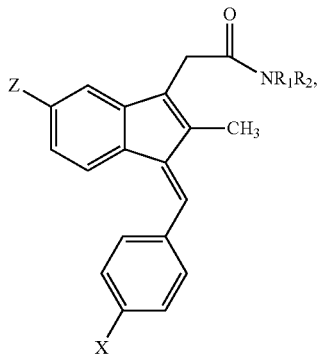

and pharmaceutically acceptable salts thereof,
wherein X is $CH_3S=O$, $CH_3S$, $HOS(=O)_2$, or $CH_3S(=O)_2$;
Z is a halogen;
$R_1$ is $(CH_2)_mY$; wherein Y is selected from the group consisting of hydrogen, alkyl, amino, aminoalkyl, and a substituted or unsubstituted 5 or 6 member ring;
$R_2$ is $(CH_2)_mW$; wherein W is selected from the group consisting of amino, aminoalkyl, and a substituted or unsubstituted 5 or 6 member ring;
or wherein both $R_1$ and $R_2$ are interconnected and connected to the nitrogen to form a saturated or unsaturated 5 or 6 member ring, which can optionally contain a further hetero atom and can optionally be substituted.

The substituted or unsubstituted 5 or 6 member ring group for Y and W can be a saturated or unsaturated ring and includes carbon, and optionally a heteroatom such as N or O;
and m is a whole number integer from 0 to 8, more typically 1 to 8 and even more typically 2-4.

Another aspect of the present disclosure relates to pharmaceutical compositions containing the above-disclosed compounds. Also disclosed are methods of using the compounds of the present disclosure in precancerous conditions and cancer in a mammal.

Another aspect of this disclosure is concerned with methods of using the compounds in treating chronic inflammatory diseases such as inflammatory bowel disease and certain neurodegenerative diseases including Alzheimer's disease.

A still further aspect of this disclosure is concerned with a method for preparing the above-disclosed compounds.

In particular, the present compounds can be produced by reacting sulindac with a compound represented by the formula:

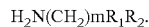

$H_2N(CH_2)mR_1R_2$.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF DRAWINGS

FIGS. 1A and 1B show growth inhibitory activity of derivatives according to the present disclosure compared with sulindac against Human HT29 colon tumor cells.

FIG. 2 shows growth inhibitory activity of a derivative according to the present disclosure against a panel of histologically diverse tumor cell types.

FIGS. 3A and 3B show cytostatic and cytotoxic activity, respectively, of a derivative according to the present disclosure compared with sulindac sulfide.

FIG. 4 shows the oral bioavailability of a derivative according to the present disclosure.

FIGS. 5A and 5B show the reduced toxicity of a derivative according to the present disclosure in mice relative to sulindac.

FIG. 6 shows antitumor activity of a derivative according to the present disclosure in athymic nude mice that were subcutaneously implanted with human colon HT29 colon tumor cells.

BEST AND VARIOUS MODES

The present disclosure is concerned with novel derivatives of sulindac represented by the formula:

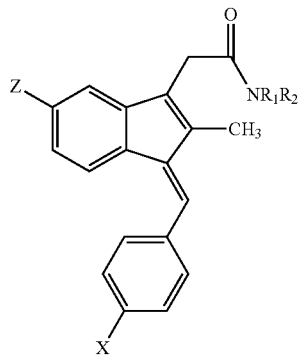

and pharmaceutically acceptable salts thereof, wherein X is $CH_3S=O$, $CH_3S$, $HOS(=O)_2$, or $CH_3S(=O)_2$; and more typically X is $CH_3S=O$, $CH_3S$, or $HOS(=O)_2$;

Z is a halogen; and more typically Z is fluorine;

$R_1$ is $(CH_2)_mY$; wherein Y is selected from the group consisting of hydrogen, alkyl, amino, aminoalkyl, and a substituted or unsubstituted 5 or 6 member ring;

$R_2$ is $(CH_2)_mW$; wherein W is selected from the group consisting of amino, aminoalkyl, and a substituted or unsubstituted 5 or 6 member ring;

or wherein both $R_1$ and $R_2$ are interconnected and connected to the nitrogen to form a saturated or unsaturated 5 or 6 member ring, which can optionally contain a further hetero atom and can optionally be substituted.

The substituted or unsubstituted 5 or 6 member ring group for Y and W can be a saturated or unsaturated ring and includes carbon, and optionally a heteroatom such as N or O m is a whole number integer from 0 to 8, more typically 1 to 8 and even more typically 2-4.

Examples of 5 and 6 member ring groups are phenyl; N-heterocyclo groups such as pyrrolidinyl, piperidinyl, piperazinyl, pyridinyl, pyrrolyl, pyrazolyl, pyrazinyl pyrimidinyl, pyridazinyl, imidazoyl and imidazolidinyl; O-heterocyclo groups such as furanyl and pyranyl; heterocyclo groups containing both N and O such as morpholinyl. When substituted these groups are typically substituted with an alkyl group, amino group or aminoalkyl group. It is understood that when the Y and/or W moieties area substituted 5 or 6 member ring group the substitution is in a position other than that connected to the $(CH_2)_m$ or to the amido N atom.

The alkyl group typically contains 1-12 carbon atoms. The alkyl group more typically contains 1-4 carbon atoms. Examples of suitable alkyl groups include methyl, ethyl and propyl. Examples branched alkyl groups include isopropyl and t-butyl. Examples of alkyl substituted aromatic groups (aralkyl) are phenyl $C_{1-3}$ alkyl and benzyl. Examples of aminoalkyl groups are aminomethyl, aminodimethyl, aminoethyl, aminodiethyl, aminopropyl and aminodipropyl.

Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic, for example p-toluenesulfonic acid.

Compounds according to the present disclosure can be prepared by known methods such as disclosed in March's Advanced Organic Chemistry, Reactions, Mechanisms and Structure, Fifth Ed. John Wiley & Sons, Inc, 2001, Chapter 10, pp 506-512, disclosure of which is incorporated herein by reference.

It has been found according to the present disclosure that compounds disclosed are surprisingly and advantageously useful in treating mammalian cancer, especially human colorectal cancer. For example, a dimethylaminoethylamide derivative of sulindac, referred to here as SRI 21004, has shown potent in vitro growth inhibitory activity against human colon tumor cells. SRI 21004 and a sulfide derivative (N-[2-(Dimethylamino)ethyl]-5-fluoro-2-methyl-1-[[4-(methylsulfide)phenyl]methylene]-1H-indene-3-acetamide, SRI 21009) display cytotoxity $IC_{50}$ values (50% inhibitory concentration) of 29.18 and 1.47 µM, respectively, which compares to $IC_{50}$ values of 479.40 and 71.22 µM for sulindac and its sulfide metabolite, respectively. This observation was unexpected since the chemical modification resulted in reduced cyclooxygenase (COX), Types 1 and 2, inhibitory activity which is widely believed to be responsible for the antineoplastic activity of sulindac. However, COX inhibition and depletion of physiologically important prostaglandins is responsible for the toxicity of NSAIDs and COX-2 selective inhibitors (i.e., celecoxib and rofecoxib), and effectively limits their utility for cancer applications that require chronic exposure and high dosages. Compounds disclosed herein are deemed to have safety and efficacy advantages over NSAIDs and COX-2 selective inhibitors for cancer and possibly other indications involving chronic inflammation. These toxicities include gastrointestinal, renal and hematological disturbances which results from COX-1 inhibition as well as cardiovascular toxicity which likely results from COX-2 inhibition. In addition, the modifications of this disclosure have the potential to display reduced hepatic toxicity which is a particular problem for sulindac and sulindac sulfone (exisulind).

The chemical modification according to this disclosure is to the carboxylic acid moiety of sulindac and is especially useful since the literature teaches that COX inhibition is necessary for the anticancer activity of NSAIDs and that COX-dependent toxicity is why NSAIDs have limitations for the treatment and prevention of cancer. The chemical modification according to this disclosure renders a net positive charge to an otherwise negatively charged species that is considered to be necessary for cyclooxygenase inhibitory activity, but was unexpectedly found to enhance anticancer activity through a cyclooxygenase-independent mechanism.

Compounds according to the present disclosure can be prepared by the following schemes.

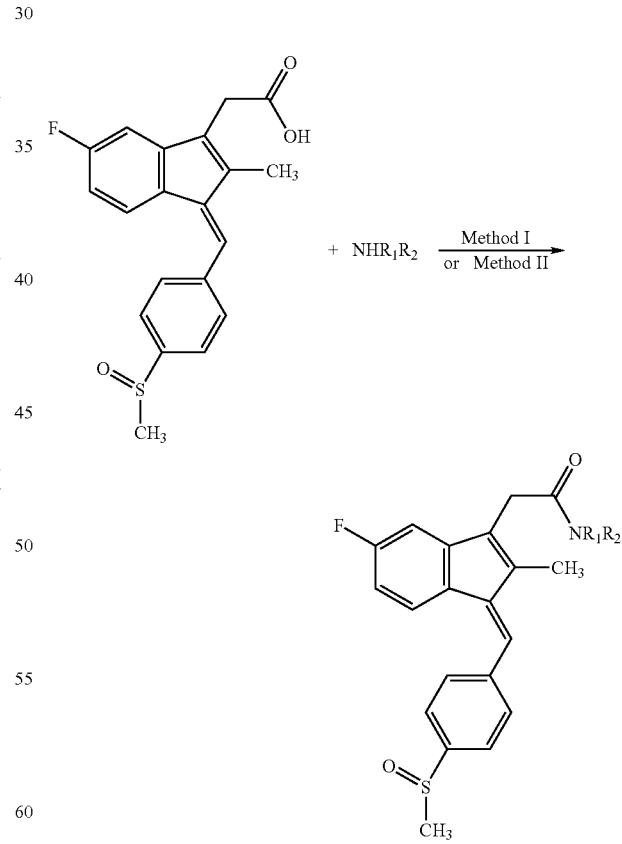

Method I. PyBoP, Pyridine, 0° C.-RT. (compounds 1-5 & 7-9)
Method II. DCC, NHS, Pyridine. (compound 6)

| | | | |
|---|---|---|---|
| 2. $R_1$ = H | $R_2$ = | [pyrrolidine with ethyl, N-CH3] | SRI# 21108 (K252-59-1) |
| 3. $R_1$ = H | $R_2$ = | [homopiperazine-propyl] | SRI# 21113 (K252-65-3) |
| 4. $R_1$ = H | $R_2$ = | [azepane-propyl] | SRI# 21114 (K252-71-1) |
| 5. $R_1$ = H | $R_2$ = | [pyridyl-propyl] | SRI# 21162 (K252-77-3) |
| 6. $R_1$ = H | $R_2$ = | [morpholine-propyl] | SRI# 21178 (K252-107-1) |
| 7. $R_1$ = H | $R_2$ = | [pyrrolidine-propyl] | SRI# 21169 (K252-85-1) |
| 8. $R_1$ = $CH_3$ | $R_2$ = | [N(CH3)2-ethyl] | SRI# 21179 (K252-113-1) |
| 9. $R_1$ = H | $R_2$ = | [NH2-propyl] | SRI# 21185 (K252-121-2) |

General Procedures for the Synthesis of Sulindac Derivatives (Compounds 1-9):
Compounds 1-5, and 7-9 are synthesized by method I and compound 6 is synthesized by method 11.

Method I:
Sulindac (60 mg, 0.17 mmol) is dissolved in anhydrous pyridine (5 mL) under an argon atmosphere and the solution is chilled in an ice/water bath (0° C.). The appropriate amine (0.033 mL, 0.25 mmol) followed by PyBOP (benzotriazole-1-yl-oxy-trispyrrolidinophosphonium hexafluorophosphate; 130 mg, 0.25 mmol) are added to the reaction. The reaction mixture is stirred at room temperature under argon overnight. Deionized water (5 mL) is added, and the reaction mixture is extracted with chloroform (2×30 mL), washed with $H_2O$ (10 mL), dried over $Na_2SO_4$, and concentrated on rotary evaporator. The resulting oil is re-dissolved in toluene and co-evaporated to remove residual pyridine. The crude product is further purified by column chromatography (60-200 mesh). The analytically pure compound is obtained by drying under vacuum overnight then at 78° C. for 4 hours.

Method II:
Sulindac (100 mg, 0.28 mmol) is dissolved in anhydrous pyridine (5 mL) under an argon atmosphere. DCC (86.66 mg, 0.42 mmol), NHS (48.34 mg, 0.42 mmol) and the amine (0.044 mL, 0.34 mmol) are added sequentially to the solution, and the reaction mixture is stirred for 2 days. The reaction is quenched by the addition of deionized water (5 mL). The precipitated material (mostly N,N'-dicyclohexylurea) is removed by filtration, and the mixture is evaporated on a rotary evaporator. The residue is co-evaporated with toluene to remove residual pyridine. The crude product is purified by column chromatography (60-200 mesh) and pure compound is dried overnight under vacuum then at 78° C. for 4 hours.

Example 1

N-[2-(Dimethylamino)ethyl]-5-fluoro-2-methyl-1-[[4-(methylsulfinyl)phenyl]methylene]-1H-indene-3-acetamide (1)

Crude product is purified by column chromatography using $CHCl_3$/MeOH+0.2% $NH_4OH$ (9:1). The product is obtained as a yellow solid in 98% yield. ESI-MS m/z: 427 [M+H]$^+$. $^1$H NMR (CDCl$_3$): δ 7.74-7.65 (2H, m, 2'-H, 3'-H), 7.17 (1H, dd, J=5.2 Hz, 8.4 Hz, 7-H), 6.88 (1H, dd, J=2.4 Hz, 8.9 Hz, 4-H), 6.59 (1H, ddd, J=2.4 Hz, 9.0 Hz, 11.0 Hz, 6-H), 6.19 (1H, br s, —NHCH$_2$CH$_2$N(CH$_3$)$_2$), 3.28 (2H, dd, J=5.7 Hz, 11.2 Hz, —NHCH$_2$CH$_2$N(CH$_3$)$_2$), 3.51 (2H, s, 3-CH$_2$), 2.81 (3H, s, 4'-CH$_3$), 2.33 (2H, t, J=6.0 Hz, —NHCH$_2$CH$_2$N (CH$_3$)$_2$), 2.13 (6H, s, N(CH$_3$)$_2$, 2.12 (3H, s, 2-CH$_3$). CHN Found: C, 67.99; H, 6.45; N, 6.60. Calcd. for $C_{24}H_{27}FN_2O_2S$; C, 67.59; H, 6.38; N, 6.57.

Example 2

2-[2-(2-Aminoethyl)-N-ethyl pyrrolidine)]-(Z)-5-fluoro-2-methyl-1-[p-(methylsulfinyl)benzylidine]-indene-3-acetamide (2)

The crude product is purified by column chromatography using CHCl$_3$/MeOH+0.2% NH$_4$OH (8:1). Yellow solid, 91% yield. ESI-MS m/z: 467 [M+H]$^+$. $^1$H NMR (DMSO-d$_6$): δ 8.10 (1H, t, J=4.2 Hz, —NHCH$_2$CH$_2$), 7.79 (1H, d, J=8.4 Hz, 3'-H), 7.71 (1H, d, J=8.2 Hz, 2'-H), 7.36 (1H, s, 8-H), 6.71 (1H, dd, J=5.4 Hz, 8.5 Hz, 7-H), 3.41 (2H, s, 1-CH$_2$), 3.12-3.06 (2H, m, —NHCH$_2$CH$_2$), 2.88-2.79 (1H, m, 2''-H), 2.82 (3H, s, 4'-CH$_3$), 2.18 (3H, s, 2-CH$_3$), 2.12 (3H, s, N—CH$_3$), 2.00-1.91 (3H, m, 3''-H$_a$, 5''-CH$_2$), 1.91-1.68 (2H, m, 3''-H$_b$), 1.68-1.50 (2H, m, —NHCH$_2$CH$_b$, 4''H$_b$), 1.40-1.07 (2H, m, —NHCH$_2$CH$_a$, 4''-H$_a$). CHN Found: C, 67.62; H, 6.48; N, 6.22. Calcd. for $C_{27}H_{31}FN_2O_2S$. 0.8 H$_2$O; C, 67.40; H, 6.83; N, 5.82.

Example 3

5-Fluoro-2-methyl-1-[[4-(methylsulfinyl)phenyl]methylene]-N-[2-(1-piperazinyl)ethyl]-1H-indene-3-acetamide (3)

The crude product is purified by column chromatography using CHCl$_3$/MeOH+0.2% NH$_4$OH (4:1) and further purified by preparative TLC using CHCl$_3$/MeOH+0.2% NH$_4$OH (5:1). Yellow solid, 58% yield. ESI-MS m/z: 468 [M+H]$^+$. $^1$H NMR (DMSO-d$_6$): δ 7.97 (1H, t, J=4.2 Hz, —NHCH$_2$CH$_2$), 7.80 (2H, d, J=8.4 Hz, 3'-H, 5'-H), 7.72 (2H, d, J=8.2 Hz, 2'-H, 6'-H), 7.35 (1H, s, 8-H), 7.15 (1H, dd, J=5.3 Hz, 8.4 Hz, 7'-H), 7.10 (1H, dd, J=2.4 Hz, 9.3 Hz, 4-H), 6.71 (1H, ddd, J=2.4 Hz, 9.6 Hz, 11.8 Hz, 6-H), 3.43 (2H, s, 1-CH$_2$), 3.16 (2H, dd, J=5.94 Hz, 11.9 Hz, —NHCH$_2$CH$_2$), 2.66 (4H, t, J=4.7 Hz, 3''-H & 5''-H), 2.51-2.30 (6H, m, —NHCH$_2$CH$_2$, 2''-H & 6''-H), 2.18 (3H, s, 2-CH$_3$) CHN Found: C, 63.53; H, 6.46; N, 8.53. Calcd. for $C_{26}H_{30}FN_3O_2S.1.3H_2O$; C, 63.60; H, 6.69; N, 8.55.

Example 4

5-Fluoro-2-methyl-1-[[4-(methylsulfinyl)phenyl]methylene]-N-[2-(1-piperidinyl)ethyl]-1H-indene-3-acetamide (4)

The crude product is purified by column chromatography using CHCl$_3$/MeOH (9:1). Yellow solid, 89% yield. ESI-MS m/z: 467 [M+H]$^+$. $^1$H NMR (DMSO-d$_6$): δ 7.95 (1H, t, J=4.4 Hz, —NHCH$_2$CH$_2$), 7.80 (2H, d, J=8.4 Hz, 3'-H, 5'-H), 7.71 (2H, d, J=8.4 Hz, 2'-H, 6'-H), 7.35 (1H, s, 8-H), 7.15 (1H, dd, J=5.4 Hz, 8.5 Hz, 7'-H), 7.10 (1H, dd, J=2.5 Hz, 9.5 Hz, 4-H), 6.71 (1H, ddd, J=2.4 Hz, 9.6 Hz, 11.0 Hz, 6-H), 3.43 (2H, s, 1-CH$_2$), 3.16 (2H, dd, J=5.0 Hz, 11.0 Hz, —NHCH$_2$CH$_2$), 2.82 (3H, s, 4'-CH$_3$), 2.40-2.36 (6H, m, —NHCH$_2$CH$_2$, 2"-H$_2$, 5"-H$_2$), 2.18 (3H, s, 2-CH$_3$), 1.44-1.31 (6H, m, 3"-H$_2$, 4"-H$_2$, 5"-H$_2$). CHN Found: C, 67.82; H, 6.51; N, 5.78. Calcd. for C$_{27}$H$_{31}$FN$_2$O$_2$S.0.7H$_2$O; C, 67.67; H, 6.81; N, 5.84.

Example 5

5-Fluoro-2-methyl-1-[[4-(methylsulfinyl)phenyl]methylene]-N-[2-(3-pyridinyl)ethyl]-1H-indene-3-acetamide (5)

The crude product is purified by column chromatography using CHCl$_3$/MeOH (95:5) and further purified by preparative TLC using CHCl$_3$/MeOH (98:2). Yellow solid, 62% yield. ESI-MS m/z: 461[M+H]$^+$. $^1$H NMR (DMSO-d$_6$): δ 8.38-8.42 (2H, m, 4"-H & 6"-H), 8.17 (1H, t, J=4.4 Hz, —NHCH$_2$CH$_2$), 7.78 (2H, d, 3'-H & 5'-H), 7.72 (2H, d, 2'-H & 6'-H), 7.60-7.56 (1H, m, 2"-H), 7.34 (1H, s, 8-H), 7.27-7.23 (1H, m, 3"-H), 7.16 (1H, dd, J=5.3 Hz, 8.4 Hz, 7-H), 6.70 (1H, ddd, J=2.4 Hz, 9.5 Hz, 11.0 Hz, 6-H), 3.40 (2H, s, 1-CH$_2$), 2.31-3.26 (2H, m, —NHCH$_2$CH$_2$), 2.82 (3H, s, 2-CH$_3$), 2.74 (2H, t, J=6.8 Hz, —NHCH$_2$CH$_2$), 2.15 (3H, s, 4'-CH$_3$): CHN Found: C, 69.48; H, 5.43; N, 5.87. Calcd. for C$_{27}$H$_{25}$FN$_2$O$_2$S.0.3H$_2$O; C, 69.60; H, 5.54; N, 6.01.

Example 6

5-Fluoro-2-methyl-1-[[4-(methylsulfinyl)phenyl]methylene]-N-[2-(4-morpholinyl)ethyl]-1H-indene-3-acetamide (6)

The crude product is purified by column chromatography using CHCl$_3$/MeOH (95:5). Yellow solid, 75% yield. ESI-MS m/z: 469 [M+H]$^+$. $^1$H NMR (DMSO-d$_6$): δ 8.00 (1H, t, J=5.0 Hz, NHCH$_2$CH$_2$), 7.79 (2H, d, J=8.5 Hz, 3'-H, 5'-H), 7.71 (2H, d, J=8.2 Hz, 2'-H & 6'-H), 7.35 (1H, s, 8-H), 7.15 (1H, dd, J=5.2 Hz, 8.4 Hz, 7-H), 7.10 (1H, dd, J=2.4 Hz, 9.4 Hz, 4-H), 6.71 (1H, ddd, J=2.5 Hz, 9.6 Hz, 11.1 Hz, 6-H), 3.52 (4H, t, J=4.6 Hz, 3"-H, 4"-H), 3.43 (2H, s, 1-CH$_2$), 3.21-3.15 (2H, m, —NHCH$_2$CH$_2$), 2.82 (3H, s, 4'-CH$_3$), 2.35-2.30 (6H, m, 2"-H, 5"-H, —NHCH$_2$CH$_2$), 2.18 (3H, s, 2-CH$_3$). CHN Found: C, 65.81; H, 5.95; N, 5.83. Calcd. for C$_{26}$H$_{29}$FN$_2$O$_3$S.0.4H$_2$O; C, 65.64; H, 6.31; N, 5.89.

Example 7

5-Fluoro-2-methyl-1-[[4-(methylsulfinyl)phenyl]methylene]-N-[2-(1-pyrrolidinyl)ethyl]-1H-indene-3-acetamide (7)

The crude product is purified by column chromatography using CHCl$_3$/MeOH (9:1)+0.2% NH$_4$OH. Yellow solid, 95% yield. ESI-MS m/z: 453 [M+H]$^+$. $^1$H NMR (DMSO-d$_6$): δ 8.12 (1H, t, J=5.0 Hz, NHCH$_2$CH$_2$), 7.78 (2H, d, J=8.4 Hz, 3'-H, 5'-H), 7.71 (2H, d, J=8.2 Hz, 2'-H, 6'-H), 7.35 (1H, s, 8-H), 7.18-7.09 (2H, m, 4-H, 7-H), 6.70 (1H, ddd, J=2.5 Hz, 9.5 Hz, 10.9 Hz, 6-H), 3.44 (2H, s, 1-CH$_2$), 3.20 2H, dd J=6.6 Hz, 9.5 Hz, —NHCH$_2$CH$_2$), 2.82 (3H, s, 4'-CH$_3$), 2.54-2.49 (4H, m, 3"-H, 4"-H, —NHCH$_2$CH$_2$), 2.18 (3H, s, 2-CH$_3$), 1.69 (4H, s, 2"-H&5"-H). CHN Found: C, 66.59; H, 6.22; N, 6.04. Calcd. for C$_{26}$H$_{29}$FN$_2$O$_2$S.0.8H$_2$O; C, 66.87; H, 6.60; N, 6.00.

Example 8

N,2-Dimethyl-N-[2-(dimethylamino)ethyl]-5-fluoro-1-[[4-ethylsulfinyl)phenyl]methylene]-1H-indene-3-acetamide (8)

The crude product is purified by column chromatography using CHCl$_3$/MeOH (9:1). Yellow solid, 62% yield. ESI-MS m/z: 441 [M+H]$^+$. $^1$H NMR (DMSO-d$_6$) The partial double bond character of the amide bond gives rise two sets of resonances: δ 7.78 (2H, d, J=8.4 Hz, 3'-H, 5'-H), 7.72 (2H, d, J=8.5 Hz, 2'-H, 6'-H), 7.35 (1H, s, 8-H), 7.15 (1H, dd, J=5.5 Hz, 8.46 Hz, 7-H), 7.01-6.95 (1H, m, 4-H), 6.71 (1H, ddd, J=2.5 Hz, 9.5 Hz, 10.9 Hz, 6-H), 3.72 & 3.65 (2H, s, 1-CH$_2$), 3.47 & 3.39 (2H, t, J=5.7 Hz, —NHCH$_2$CH$_2$), 3.08 & 2.84 (3H, s, —NCH$_3$), 2.82 (3H, s, 4'-CH$_3$), 2.42 & 2.32 (2H, t, J=6.7 Hz, —NHCH$_2$CH$_2$ s, 2-C), 2.20 (3H, H$_3$s, —N(C), 2.13 (6H, H$_3$)$_2$). CHN Found: C, 67.41; H, 6.51; N, 6.29. Calcd. for C$_{25}$H$_{29}$FN$_2$O$_2$S.0.3H$_2$O; C, 67.33; H, 6.69; N, 6.28.

Example 9

N-(2-Aminoethyl)-5-fluoro-2-methyl-1-[[4-(methylsulfinyl)phenyl]methylene]-1H-indene-3-acetamide (9)

The crude product is purified by column chromatography using CHCl$_3$/MeOH+0.2% NH$_4$OH (9:1). The product was obtained as a yellow solid in 95% yield. ESI-MS m/z: 399 [M+H]$^+$. $^1$H NMR (DMSO-d$_6$): δ 8.09 (1H, t, J=5.2 Hz, NHCH$_2$CH$_2$NH$_2$), 7.78 (2H, d, J=8.5 Hz, 3'-H, 5'-H), 7.72 (2H, d, J=8.1 Hz, 2'-H, 6'-H), 7.35 (1H, s, 8-H), 7.18-7.10 (2H, m, 4-H, 7-H), 6.70 (1H, ddd, J=2.4 Hz, 9.7 Hz, 11.1 Hz, 6-H), 3.43 (2H, s, 3-CH$_2$), 3.05 (2H, dd, J=6.1 Hz, 11.9 Hz, —NHCH$_2$CH$_2$NH$_2$), 2.82 (3H, s, 4'-CH$_3$), 2.57 (2H, t, J=6.3 Hz, —NHCH$_2$CH$_2$NH$_2$), 2.18 (3H, s, 2-CH$_3$). CHN Found: C, 62.47; H, 6.33; N, 6.33. Calcd. for C$_{22}$H$_{23}$FN$_2$O$_2$S.1.4H$_2$O; C, 62.36; H, 6.14; N, 6.61.

Example 10

N-[2-(Dimethylamino)ethyl]-5-fluoro-2-methyl-1-[[4-(methylthio)phenyl]methylene]-1H-indene-3-acetamide (General method: Olah et al. *Synthesis* 1978 137.):

Triphenylphosphine (0.502 g, 1.913 mmol) and I$_2$ (0.486 g, 1.913 mmol) are stirred together in acetonitrile (5 mL) until a yellow slurry is obtained. A solution of the sulfoxide from example (0.068 g, 0.16 mol) in acetonitrile (5 mL) is added to the yellow slurry followed by the addition of powdered NaI (0.358 g, 2.39 mmol). The reaction mixture is stirred under Argon overnight at room temperature. The reaction mixture is heated gently for 6 h in an attempt to push to completion, and then left at room temperature overnight under Argon. The reaction is diluted with ether (250 mL), washed with Na$_2$S$_2$O$_3$ saturated solution, 5% NaHCO$_3$, H$_2$O, concentrated, re-dissolved in CHCl$_3$, dried over Na$_2$SO$_4$ and concentrated to a yellow residue. The crude material is purified by column chromatography using chloroform/methanol 20:1 to pack and elute the column of silica gel (230-400 mesh). A yellow solid is obtained in 44% yield (29 mg). FABMS m/z: 411 (M+H)$^+$. $^1$H NMR: (CDCl$_3$) H29389 δ 2.11 (6H, s, N(CH$_3$)$_2$, 2.20 (3H, s, 2-CH$_3$), 2.31 (2H, t, —NHCH$_2$CH$_2$N(CH$_3$)$_2$, J=5.94 Hz), 2.55 (3H, s, 4'-CH$_3$), 3.27 (2H, dd, —NHCH$_2$CH$_2$N(CH$_3$)$_2$, J=5.82 Hz, 11.42 Hz), 3.51 (2H, s, 3-CH$_2$), 6.17 (1H, br. s, —NHCH$_2$CH$_2$N(CH$_3$)$_2$), 6.60 (1H, ddd, 6-H), 6.87 (1H, dd, 4-H, J=2.41 Hz, 9.0 Hz), 7.16 (1H, s, 10-H), 7.31-7.26 (1H, m, 6'-H), 7.38 (1H, dd, 7-H, J=5.27 Hz, 8.46 Hz), 7.44 (2H, d, 3'-H & 5'-H); the spectrum supports submitted structure with some H$_2$O present. CHN(C$_{24}$H$_{27}$N$_2$OSF) Found: C, 69.84; H, 6.77; N, 6.89. Calcd. C, 70.21; H, 6.63; N, 6.82.

In addition, the following compounds according to the present disclosure can be prepared by the following schemes:

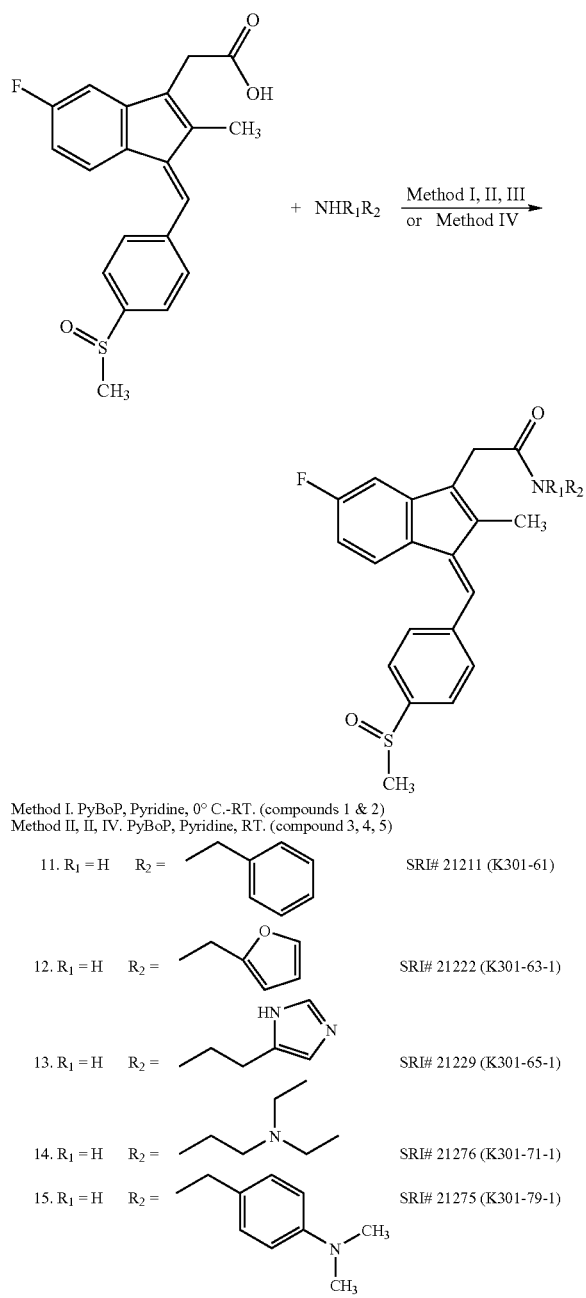

General Procedures for the Synthesis of Sulindac Derivatives (Compounds 11-15):

Compounds 11 and 12 are synthesized by method I, compound 13 is synthesized by method II, compound 14 is synthesized by method III, and compound 15 is synthesized by method IV.

Method I:

Sulindac (100 mg, 0.28 mmol) is dissolved in anhydrous pyridine (5 mL) under an argon atmosphere and solution is chilled in ice/water bath (~0° C.). Amine (0.045 mL, 0.42 mmol) followed by PyBOP (benzotriazole-1-yl-oxy-trispyr-rolidinophosphonium hexafluorophosphate; 219 mg, 0.42 mmol) are added to the reaction. The reaction mixture is stirred at room temperature under argon overnight. Deionized water (5 mL) is added and reaction mixture is extracted with chloroform (2×30 mL), washed with $H_2O$ (10 mL), dried over $Na_2SO_4$, concentrated on rotary evaporator. It is re-dissolved in toluene and co-evaporated to remove residual pyridine. The crude product is purified by column chromatography (60-200 mesh). The pure compound is dried under vacuum for at least 48 hours.

Method II:

Sulindac (100 mg, 0.28 mmol) is dissolved in anhydrous pyridine (5 mL) under an argon atmosphere. Amine (77 mg, 0.42 mmol) followed by PyBOP (benzotriazole-1-yl-oxy-trispyrrolidinophosphonium hexafluorophosphate; 219 mg, 0.42 mmol) are added to the reaction. The reaction mixture is stirred at room temperature under argon overnight. Amine (26 mg, 0.14 mmol) is added to the reaction to increase the sulindac to amine ration 1:2. Reaction mixture is stirred at room temperature under argon for 72 hours. Deionized water (5 mL) is added to the reaction mixture to quench the reaction. The reaction mixture is co-evaporated with toluene to remove residual pyridine. The crude product is purified by column chromatography (60-200 mesh). The pure compound is dried under vacuum for at least 48 hours.

Method III:

Sulindac (100 mg, 0.28 mmol) is dissolved in anhydrous pyridine (5 mL) under an argon atmosphere. Amine (0.06 mL, 0.42 mmol) followed by PyBOP (benzotriazole-1-yl-oxy-trispyrrolidinophosphonium hexafluorophosphate; 219 mg, 0.42 mmol) are added to the reaction. Reaction mixture is stirred at room temperature under argon for 72 hours. Deionized water (5 mL) is added and reaction mixture is extracted with chloroform (2×30 mL), washed with $H_2O$ (10 mL), dried over $Na_2SO_4$, concentrated on rotary evaporator. It is re-dissolved in toluene and co-evaporated to remove residual pyridine. The crude compound is dried under vacuum for 72 hours. The crude product is purified by column chromatography (60-200 mesh). The pure product is co-evaporated with ethanol (3×50 mL). Pure compound is dried on drying pistol overnight.

Method IV:

Sulindac (100 mg, 0.28 mmol) is dissolved in anhydrous pyridine (5 mL) under an argon atmosphere. Amine (95 mg, 0.42 mmol) followed by PyBOP (benzotriazole-1-yl-oxy-trispyrrolidinophosphonium hexafluorophosphate; 219 mg, 0.42 mmol) are added to the reaction. Reaction mixture is stirred at room temperature under argon for two weeks. Deionized water (5 mL) is added to the reaction mixture to quench the reaction. The reaction mixture is co-evaporated with toluene to remove residual pyridine. The crude product is purified by column chromatography (60-200 mesh). The pure compound is co-evaporated with ethanol (2×50 mL). Pure compound is dried on drying pistol overnight.

Example 11

5-Fluoro-2-methyl-1-[[4-(methylsulfinyl)phenyl] methylene]-N-(phenylmethyl)-1H-indene-3-acetamide (11)

Crude product is purified by column chromatography using $CHCl_3$/MeOH (98:2). The product is obtained as yellow solid in 91% yield. ESI-MS m/z: 446 [M+H]+. $^1$H NMR (DMSO-$d_6$): δ 8.64 (1H, t, J=6.2 Hz, —NHCH$_2$), 7.79 (2H, d, J=8.3 Hz, 3'-H, 5'-H), 7.72 (2H, d, J=8.3 Hz, 2'-H, 6'-H), 7.35 (1H, s, 8-H), 7.32-7.23 (5H, m, C$_6$H$_5$), 7.17 (1H, dd, J=5.2 Hz, 8.4 Hz, 7-H), 7.13 (1H, dd, J=2.5 Hz, 9.5 Hz, 4-H), 6.71 (1H, ddd, J=2.5 Hz, 8.5 Hz, 9.4 Hz, 6-H), 4.29 (2H, d, J=5.8

Hz, —NHCH$_2$), 3.51 (2H, s, 3-CH$_2$), 2.82 (3H, s, CH$_3$SO—), 2.20 (3H, s, 2-CH$_3$). CHN Found: C, 71.48; H, 5.36; N, 3.22. Calcd. for C$_{27}$H$_{24}$FNO$_2$S.0.4H$_2$O; C, 71.63; H, 5.52; N, 3.09.

Example 12

5-Fluoro-N-(2-furanylmethyl)-2-methyl-1-[[4-(methylsulfinyl)phenyl]methylene]-1H-indene-3-acetamide (12)

Crude product is purified by column chromatography using CHCl$_3$/MeOH (95:5) and further purified by preparative TLC using CHCl$_3$/MeOH (95:5). Yellow solid, 34% yield. ESI-MS m/z: 436[M+H]$^+$. $^1$H NMR (DMSO-d$_6$): δ 8.61 (1H, t, J=5.3 Hz, —NHCH$_2$), 7.79 (2H, d, J=8.3 Hz, 3'-H, 5'-H), 7.72 (2H, d, J=8.3 Hz, 2'-H, 6'-H), 7.57 (1H, dd, J=0.9 Hz, 1.9 Hz, 5"-H 7.35 (1H, s, 8-H), 7.16 (1H, dd, J=5.3 Hz, 8.4 Hz, 7-H), 7.11 (1H, dd, J=2.4 Hz, 9.4 Hz, 4-H), 6.71 (1H, ddd, J=2.5 Hz, 8.4 Hz, 9.4 Hz, 6-H), 6.39 (1H, dd, J=1.9 Hz, 3.2 Hz, 4"-H), 6.22 (1H, dd, J=0.8 Hz, 3.2 Hz, 3"-H), 4.28 (2H, d, J=5.6 Hz, —NHCH$_2$), 3.47 (2H, s, 3-CH$_2$), 2.82 (3H, s, CH$_3$SO—), 2.18 3H, s, 2-CH$_3$ CHN Found: C, 66.72; H, 4.88; N, 3.09. Calcd. for C$_{25}$H$_{22}$FNO$_3$S.0.75H$_2$O; C, 66.87; H, 5.27; N, 3.12.

Example 13

5-Fluoro-N-[2-(4-imidazolyl)ethyl]-2-methyl-1-[[4-(methylsulfinyl)phenyl]methylene-1H-indene-3-acetamide (13)

Crude product is purified by column chromatography using CHCl$_3$/MeOH+0.2% NH$_4$OH (9:1) and further purified by preparative TLC using CHCl$_3$/MeOH+0.2% NH$_4$OH (8:1). Yellow solid, 54% yield of reacted material, 31% yield. ESI-MS m/z: 450[M+H]$^+$. $^1$H NMR (DMSO-d$_6$ The imidazole ring gives rise two sets of resonances δ 8.16 (1H, br t, J=5.3 Hz, —NHCH$_2$CH$_2$), 7.79 (2H, d, J=8.4 Hz, 3'-H, 5'-H), 7.72 (2H, d, J=8.4 Hz, 2'-H, 6'-H), 7.50 (1H, br s, 2"-H), 7.35 (1H, s, 8-H), 7.16 (1H, dd, J=5.3 Hz, 8.4 Hz, 7-H), 7.09 (1H, dd, J=2.5 Hz, 9.4 Hz, 4-H), 6.83 (1H, br s, 4"-H), 6.71 (1H, ddd, J=2.5 Hz, 8.4 Hz, 9.5 Hz, 6-H), 3.42 (2H, s, 3-CH$_2$), 3.26 (2H, m, —NHCH$_2$CH$_2$), 2.82 (3H, s, CH$_3$SO—), 2.65 (2H, m, —NHCH$_2$CH$_2$), 2.17. □□, s, 2-CH$_3$} CHN Found: C, 64.22; H, 5.37; N, 8.71. Calcd. for C$_{25}$H$_{24}$FN$_3$O$_2$S.1.0H$_2$O; C, 64.22; H, 5.60; N, 8.99.

Example 14

5-Fluoro-N-[2-(N,N-diethylamino)ethyl]-2-methyl-1-[[4-(methylsulfinyl)phenyl]methylene-1H-indene-3-acetamide (14)

Crude product is purified by column chromatography using CHCl$_3$/MeOH (95:5) and further purified by preparative TLC using CHCl$_3$/MeOH+1.0% NH$_4$OH (9:1) and by preparative TLC using CHCl$_3$/MeOH+1.0% NH$_4$OH (7:1). Yellow solid, 28% yield. ESI-MS m/z: 455[M+H]$^+$. $^1$H NMR (DMSO-d$_6$) δ 7.92 (1H, t, J=5.3 Hz, —NHCH$_2$CH$_2$), 7.79 (2H, d, J=8.4 Hz, 3'-H, 5'-H), 7.71 (2H, d, J=8.4 Hz, 2'-H, 6'-H), 7.35 (1H, s, 8-H), 7.16 (1H, dd, J=5.2 Hz, 8.4 Hz, 7-H), 7.10 (1H, dd, J=2.5 Hz, 9.4 Hz, 4-H), 6.72 (1H, ddd, J=2.5 Hz, 8.4 Hz, 9.4 Hz, 6-H), 3.43 (2H, s, 3-CH$_2$), 3.12 (2H, m, —NHCH$_2$CH$_2$), 2.82 (3H, s, CH$_3$SO—), 2.44 (4H, m, —N(CH$_2$CH$_3$)$_2$), 2.41 (2H, m, —NHCH$_2$CH$_2$), 2.18 3H, s, 2-CH$_3$), 0.91 (6H, t, J=7.1 Hz, —N(CH$_2$CH$_3$)$_2$} CHN Found: C, 66.67; H, 6.98; N, 5.91. Calcd. for C$_{26}$H$_{31}$FN$_2$O$_2$S.0.8H$_2$O; C, 66.58; H, 7.01; N, 5.97.

Example 15

N-[[4-(Dimethylamino)phenyl]methyl]-5-fluoro-2-methyl-1-[[4-(methylsulfinyl)phenyl]methylene]-1H-indene-3-acetamide (15)

Crude product is purified by column chromatography using CHCl$_3$/MeOH+1.0% NH$_4$OH (95:5) and further purified by preparative TLC using CHCl$_3$/MeOH (9:1). Yellow solid, 36% yield of reacted material, 26% yield. ESI-MS m/z: 489[M+H]$^+$. $^1$H NMR (DMSO-d$_6$) δ 8.48 (1H, t, J=5.3 Hz, —NHCH$_2$), 7.79 (2H, d, J=8.4 Hz, 3'-H, 5'-H), 7.72 (2H, d, J=8.4 Hz, 2'-H, 6'-H), 7.35 (1H, s, 8-H), 7.16 (1H, dd, J=5.3 Hz, 8.4 Hz, 7-H), 7.11 (1H, dd, J=2.6 Hz, 9.6 Hz, 4-H), 7.08 (2H, m, 2"-H), 6.71 (1H, ddd, J=2.4 Hz, 8.4 Hz, 9.5 Hz, 6-H), 6.66 (2H, m, 3"-H), 4.15 (2H, d, J=5.6 Hz, —NHCH$_2$), 3.47 (2H, s, 1-CH$_2$), 2.85 (6H, s, —N(CH$_3$)$_2$) 2.82 (3H, s, CH$_3$SO—), 2.19 3H, s, 2-CH$_3$} CHN Found: C, 71.07; H, 6.06; N, 5.70. Calcd. for C$_{29}$H$_{29}$FN$_2$O$_2$S; C, 71.29; H, 5.98; N, 5.73.

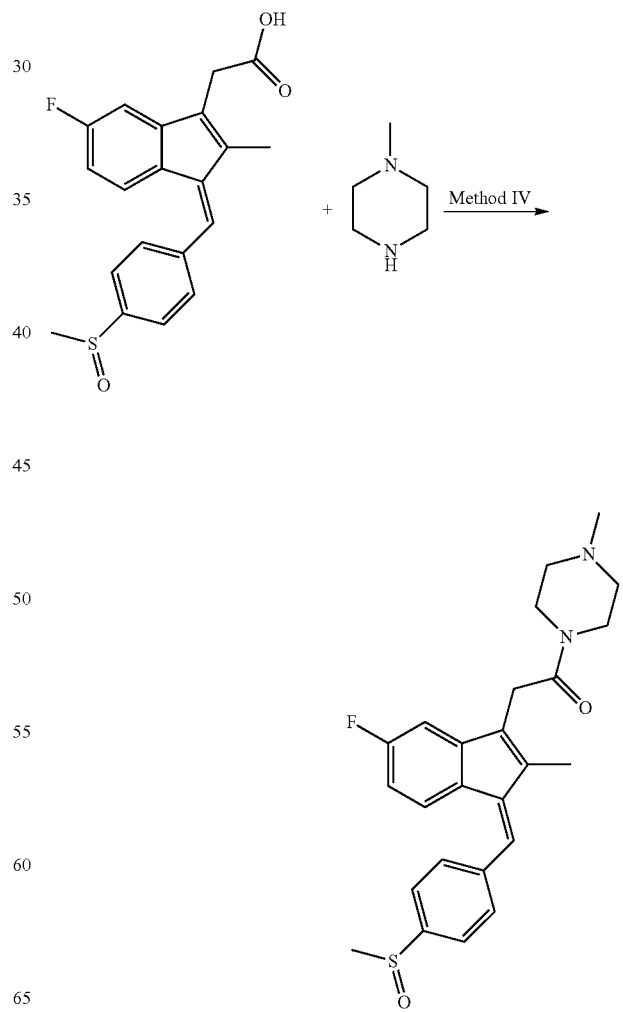

(SRI # 21387)

Example 16

Ethanone, 2-[5-fluoro-2-methyl-1-[[4-(methylsulfinyl)phenyl]methylene]-1H-inden-3-yl]-1-(4-methylpiperazinyl)

Crude product was purified by column chromatography using CHCl$_3$/MeOH+0.2% NH$_4$OH (95:5). The product is obtained as a yellow solid in modest yield. ESI-MS m/z: 439.23 [M+H]$^+$. $^1$H NMR (CDCl$_3$, 300 MHz): δ 7.73-7.64 (4H, m, 2'-H, 3'-H, 5'-H, 6'-H), 7.16 (1H, dd, $^3$J=8.7 Hz, $^4$J=5.4 Hz, 7-H), 7.12 (1H, s, 8-H), 6.90 (1H, dd, $^3$J=9.0 Hz, $^4$J=2.4 Hz, 4-H), 6.58-6.51 (1H, m, 6-H), 3.69 (2H, m, CH$_2$NCH$_3$), 3.60 (2H, s, CH$_2$CO), 3.55 (2H, m, CH$_2$NCH$_3$), 2.81 (3H, s, SOCH$_3$), 2.42-2.37 (4H, m, CONCH$_2$), 2.30 (3H, s, NCH$_3$), 2.18 (3H, s, 2-CH$_3$). Anal. Calcd for C$_{25}$H$_{27}$FN$_2$O$_2$S·0.1 CH$_3$COOH: C, 65.17; H, 5.87; N, 5.63. Found: C, 64.80; H, 6.15; N, 5.74 . . . .

Compounds 17, 18, 19 are synthesized by method V and compounds 20 is synthesized by method IV.

Method V

O-(Benzotriazol-1-yl)-N,N,N',N'-tetramethyluronium hexafluorophosphate, (HBTU) (114 mg, 0.2996 mmol) is added to a solution of sulindac sulfide or sulindac (0.2497 mmol), the appropriate amine (0.2996 mmol) and Et$_3$N (0.07 mL, 0.4994 mmol) in dry acetonitrile (10 mL) at room temperature under argon atmosphere. Reaction mixture is stirred at room temperature for 30 minutes. Saturated brine (30 mL) is added to the reaction mixture and extracted with CHCl$_3$ (2×30 mL). The combined organic extracts are dried over anhydrous Na$_2$SO$_4$ and the solvent is evaporated off under reduced pressure. The crude product is purified by flash column chromatography (60-200 mesh).

Method VI

Diphenylphosphoryl azide, DPPA (0.052 mL, 0.2417 mmol) is added to a solution of sulindac sulfone (75 mg, 0.2014 mmol) and N,N-dimethylethylenediamine (0.026 mL, 0.2417 mmol) in dry DMF (2 mL) at 0° C. under argon atmosphere. Reaction mixture is allowed to room temperature and stirred overnight. Aqueous Na$_2$CO$_3$ (30 mL) is added to the reaction mixture and extracted with CHCl$_3$ (2×30 mL). The combined organic extracts are dried over anhydrous Na$_2$SO$_4$ and the solvent is evaporated off under reduced pressure. The crude product is purified by flash column chromatography (60-200 mesh).

Example 17

N-[[4-(Dimethylamino)phenyl]methyl]-(Z)-5-fluoro-2-methyl-3-[[4-(methylthio)phenyl]methylene]-1H-indene-3-acetamide Crude product is purified by column chromatography using CHCl$_3$/Petroleum ether+0.1% NH$_4$OH (4:1)). The product is obtained as a yellow solid in 98% yield. ESI-MS m/z: 473.26 [M+H]$^+$. $^1$H NMR (CDCl$_3$, 300 MHz): δ 7.45 (2H, d, $^3$J=8.1 Hz, 3'-H, 5'-H), 7.38 (1H, dd, $^3$J=8.4 Hz, $^4$J=5.1 Hz, 7-H), 7.30 (2H, dd, $^3$J=8.4 Hz, 2'-H, 6'-H), 7.14 (1H, s, 8-H), 7.03 (2H, d, J=8.7 Hz, 2''-H, 6''-H), 6.87 (1H, dd, $^3$J=9.0 Hz, $^4$J=2.4 Hz, 4-H), 6.64-6.56 (3H, m, 6-H, 3''-H, 5''-H), 5.75 (1H, bs, NH), 4.32 (2H, d, J=5.6 Hz, NH—CH$_2$—), 3.56 (2H, s, —CH$_2$—CO), 2.90 (6H, s, N(CH$_3$)$_2$), 2.54 (3H, s, —SCH$_3$), 2.17 (3H, s, 2-CH$_3$). Anal. Calcd for C$_{29}$H$_{29}$FN$_2$OS: C, 73.70; H, 6.18; N, 5.93. Found: C, 73.74; H, 6.17; N, 5.72.

Example 18

N,2-Dimethyl-(Z)-5-fluoro-2-methyl-N-[2-(methylamino)ethyl]-3-[[4-(methylthio)phenyl]methylene]]-1H-indene-3-acetamide Crude product is purified by column chromatography using CHCl$_3$/MeOH+0.1% NH$_4$OH (97:1). The product is obtained as a yellow solid in 82% yield. ESI-MS m/z: 411.26 [M+H]$^+$, 821.49 [2M+H]$^+$. $^1$H NMR (CDCl$_3$, 300 MHz): δ 7.45 (2H, d, $^3$J=8.1 Hz, 3'-H, 5'-H), 7.65 (2H, d, J=8.1 Hz, 2'-H, 6'-H), 7.15-7.10 (2H, m's, 4-H, 8-H)29 6.96-6.90 (1H, m, 7-H), 6.59-6.52 (1H, m, 6-H), 3.69, 3.62 (2H, 2s, —CH$_2$—CO), 3.55-3.46 (2H, m, N(CH$_3$)—CH$_2$), 3.09, 2.97 (3H, 2s, CO—N(CH$_3$)), 2.79-2.74 (2H, m, CH$_2$—NH(CH$_3$)), 2.54 (3H, s, —SCH$_3$), 2.45, 2.42 (3H, 2s, NHCH$_3$), 2.18 (3H, s, 2-CH$_3$). Anal. Calcd for C$_{24}$H$_{27}$FN$_2$OS·0.35H$_2$O: C, 69.15; H, 6.69; N, 6.71. Found: C, 69.00; H, 6.50; N, 6.29.

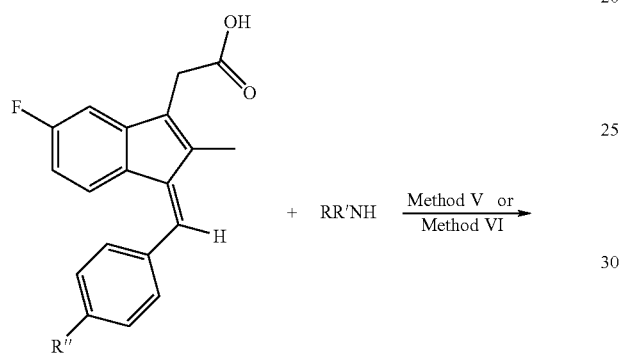

Example 19

N-[[4-(Dimethylamino)phenyl]-(Z)-5-fluoro-2-methyl-3-[[4-(methylsulfinyl)phenyl]methylene]]-1H-indene-3-acetamide Crude product is purified by column chromatography using $CHCl_3$/MeOH+0.1% $NH_4OH$ (99:1). The product is obtained as a yellow solid in 98% yield. ESI-MS m/z: 475.21 $[M+H]^+$ 949.42 $[2M+H]^+$. $^1H$ NMR ($CDCl_3$, 300 MHz): δ 7.75-7.67 (4H, m, 2'-H, 3'-H5'-H, 6'-H), 7.25 (2H, d, $^3J=9.0$ Hz, 2''-H, 6''-H), 7.22 (1H, s, 8-H), 7.20 (1H, dd, $^3J=8.4$ Hz, $^4J=5.1$ Hz, 7-H), 7.13 (1H, bs, NH), 6.95 (1H, dd, $^3J=8.7$ Hz, $^4J=2.4$ Hz, 4-H), 6.66 (2H, d, $^3J=9.0$ Hz, 3''-H, 5''-H), 6.67-6.57 (1H, m, 6-H), 3.66 (2H, s, $CH_2$—CO), 2.89 (6H, s, $N(CH_3)_2$), 2.82 (3H, s, —$SOCH_3$), 2.27 (3H, s, 2-$CH_3$). Anal. Calcd for $C_{28}H_{27}FN_2O_2S\cdot1.0H_2O$: C, 68.27; H, 5.93; N, 5.69. Found: C, 68.34; H, 5.66; N, 5.80.

Example 20

N-[2-(Dimethylamino)ethyl]-(Z)-5-fluoro-2-methyl-3-[[4-(methylsulfonyl)phenyl]methylene]]-1H-indene-3-acetamide Crude product is purified by column chromatography using $CHCl_3$/MeOH+0.1% $NH_4OH$ (49:1). The product is obtained as a yellow solid in 94% yield. ESI-MS m/z: 443.22 $[M+H]^+$. $^1H$ NMR ($CDCl_3$, 300 MHz): δ 8.02 (2H, d, $^3J=8.4$ Hz, 3'-H, 5'-H), 7.72 (2H, d, $^3J=8.7$ Hz, 2'-H, 6'-H), 7.13 (1H, s, 8-H), 7.11 (1H, dd, $^3J=8.4$ Hz, $^4J=5.1$ Hz, 7-H), 6.90 (1H, dd, $^3J=9.0$ Hz, $^4J=2.7$ Hz, 4-H), 6.61-6.54 (1H, m, 6-H), 6.31 (1H, bs, NH), 3.50 (2H, s, $CH_2$—CO), 3.30 (2H, q, J=5.7 Hz, NH—$CH_2$), 3.14 (3H, s, $SO_2CH_3$), 2.36 (2H, t, $CH_2$—N$(CH_3)_2$), 2.21 (3H, s, 2-$CH_3$), 2.16 (6H, s, $N(CH_3)_2$). Anal. Calcd for $C_{24}H_{27}FN_2O_3S\cdot0.25H_2O$: C, 64.48; H, 6.20; N, 6.27. Found: C, 64.54; H, 6.05; N, 6.29.

Example 21

N-[[4-(Dimethylamino)phenyl]-(Z)-5-fluoro-2-methyl-3-[[4-(methylthio)phenyl]methylene]]-1H-indene-3-acetamide Crude product is purified by column chromatography using 2% MeOH—$CHCl_3$+0.1% $NH_4OH$. The product is obtained as a yellow solid in 100% yield. ESI-MS m/z: 459.25 $[M+H]^+$, 917.49 $[2M+H]^+$. $^1H$ NMR ($CDCl_3$, 300 MHz): δ 7.47 (2H, d, $^3J=8.2$ Hz, 2'-H, 6'-H), 7.44 (1H, dd, $^3J=8.4$ Hz, $^4J=5.2$ Hz, 7-H), 7.31 (2H, d, $^3J=8.2$ Hz, 3'-H, 5'-H), 7.22 (2H, dd J=9.0 Hz, 2''-H, 6''-H) 7.21 (1H, s, 8-H), 7.08 (1H, bs, NH), 6.93 (1H, dd, $^3J=8.8$ Hz, $^4J=2.4$ Hz, 4-H), 6.67-6.60 (3H, overlapping m's, 3''-H, 5''-H, 6-H1), 3.66 (2H, s, $CH_2$—CO), 2.89 (6H, s, $N(CH_3)_2$), 2.56 (3H, s, —$SCH_3$), 2.26 (3H, s, 2-$CH_3$). Anal. Calcd for $C_{28}H_{27}FN_2OS\cdot0.25H_2O$: C, 72.62; H, 5.99; N, 6.05. Found: C, 72.41; H, 5.61; N, 5.74.

Experimental Results

In vitro cytotoxicity testing using the human HT29 colon tumor cell line reveals significant potency improvements of the sulindac derivatives SRI 21004 (sulfoxide) and SRI 21009 (sulfide) relative to the corresponding forms of sulindac. Growth inhibitory activity of SRI derivatives and sulindac using the tritiated thymidine incorporation assay (left panel) or the MTS cell viability assay (right panel) are shown in FIGS. 1A and 1B. Note the increased potency of SRI derivatives compared to sulindac and its sulfone and sulfide metabolites. Also note that higher concentrations of sulindac and its metabolites were required to reduce viable cell number compared to concentrations required to inhibit proliferation, which was not the case for the SRI derivatives. This indicates greater potential of the SRI derivatives to kill tumor cells compared to sulindac and its metabolites.

FIG. 2 shows growth inhibitory activity of SRI 21009 against a panel of histologically disease tumor cell types. Note the enhanced sensitivity of tumor cells derived from colorectal tumors compared with other tumor types.

FIGS. 3A and 3B show cytostatic and cytotoxic activity, respectively, of SRI 21004 compared with sulindac sulfide. Cytotoxic activity is defined as the ability the treatment to reduce cell number below the number when treatment was initiated and is an indicator of chemotherapeutic efficacy. Cytostasis is defined as the ability of the treatment to reduce cell number relative to untreated cells and is an indicator of chemopreventive efficacy. Note that SRI 21004 displays greater potential for chemotherapeutic efficacy compared with sulindac sulfide and is consistent with greater ability to kill tumor cells as indicated in FIG. 1B.

FIG. 4 shows the oral bioavailability of SRI 21009. The achievable plasma levels following the oral administration of SRI 21009 at a single dose of 200 mg/kg exceeded the $IC_{50}$ value for in vitro growth inhibition. Negligible amounts of sulindac sulfoxide, sulfone, or sulfide are detected in the plasma following SRI 21009 administration.

FIGS. 5A and 5B show the reduced toxicity of SRI 21009 in mice relative to sulindac. Following a once a day dosing schedule, the maximum tolerated dose of sulindac is estimated to be 50 mg/kg in comparison to 300 mg/kg for SRI 21009.

FIG. 6 shows antitumor activity of SRI 21009 in athymic nude mice that are subcutaneously implanted with human colon HT29 colon tumor cells. For this study, SRI 21009 is administered orally once every two days at a dose of 700 mg/kg. SRI 21009 administered at 300 mg/kg is as effective as sulindac at 50 mg/kg using a once a day dosing schedule.

Table A below shows the reduced COX-1 and COX-2 inhibitory activity of SRI 21009 in comparison to a non-selective COX inhibitor (sulindac sulfide), a COX-1 selective inhibitor (indomethacin), and a COX-2 selective inhibitor (rofecoxib). The inhibitory activity of the compounds is expressed as an $IC_{50}$ value (50% inhibitory concentration).

TABLE A

COX-1 and Cox-2 inhibitory activity of known NSAIDs and SRI 210009

| Compound | COX-1 $IC_{50}$ (μM) | COX-2 $IC_{50}$ (μM) |
|---|---|---|
| Rofecoxib | >300 | 2.7 |
| Indomethacin | 0.017 | 1.0 |
| Sulindac Sulfide | 1.8 | 6.3 |
| SRI 21009 | 1476 | 164.5 |

Additional derivatives of sulindac sulfoxide are synthesized and tested for growth inhibitory activity against human HT29 colon tumor cells are shown in Table 1 below. All derivatives are more active than sulindac sulfoxide, with several displayed comparable or greater activity compared SRI 21004.

TABLE B

| SRI Number | Chemical Name | *IC$_{50}$ value (μM) |
|---|---|---|
| na | Sulindac sulfoxide | 450.5 |
| na | Sulindac sulfide | 45.2 |
| SRI 21004 | N-[2-(Dimethylamino)ethyl]-5-fluoro-2-methyl-1-[[4-(methylsulfinyl)phenyl]methylene]-1H-indene-3-acetamide | 25.1 |
| SRI 21008 | 5-Fluoro-2-methyl-N-[(1-methyl-2-pyrrolidinyl)methyl]-1-[[4-(methylsulfinyl)phenyl]methylene]-1H-indene-3-acetamide | 18.7 |
| SRI 21113 | 5-Fluoro-2-methyl-1-[[4-(methylsulfinyl)phenyl]methylene]-N-[2-(1-piperazinyl)ethyl]-1H-indene-3-acetamide | 76.9 |
| SRI 21114 | 5-Fluoro-2-methyl-1-[[4-(methylsulfinyl)phenyl]methylene]-N-[2-(1-piperidinyl)ethyl]-1H-indene-3-acetamide | 19.7 |
| SRI 21162 | 5-Fluoro-2-methyl-1-[[4-(methylsulfinyl)phenyl]methylene]-N-[2-(3-pyridinyl)ethyl]-1H-indene-3-acetamide | 99.8 |
| SRI 21169 | 5-Fluoro-2-methyl-1-[[4-(methylsulfinyl)phenyl]methylene]-N-[2-(1-pyrrolidinyl)ethyl]-1H-indene-3-acetamide | 17.2 |
| SRI 21178 | 5-Fluoro-2-methyl-1-[[4-(methylsulfinyl)phenyl]methylene]-N-[2-(4-morpholinyl)ethyl]-1H-indene-3-acetamide | 114 |
| SRI 21179 | N,2-Dimethyl-N-[2-(dimethylamino)ethyl]-5-fluoro-1-[[4-ethylsulfinyl)phenyl]methylene]-1H-indene-3-acetamide | 19.8 |
| SRI 21185 | N-(2-Aminoethyl)-5-fluoro-2-methyl-1-[[4-(methylsulfinyl)phenyl]methylene]-1H-indene-3-acetamide | 85.2 |
| SRI 21229 | 5-Fluoro-N-[2-(4-imidazolyl)ethyl]-2-methyl-1-[[4-(methylsulfinyl)phenyl]methylene-1H-indene-3-acetamide | 32.6 |
| SRI 21275 | N-[[4-(Dimethylamino)phenyl]methyl]-5-fluoro-2-methyl-1-[[4-(methylsulfinyl)phenyl]methylene]-1H-indene-3-acetamide | 6.3 |
| SRI 21276 | 5-Fluoro-N-[2-(N,N-diethylamino)ethyl]-2-methyl-1-[[4-(methylsulfinyl)phenyl]methylene-1H-indene-3-acetamide | 18.2 |
| SRI 21009 | N-[2-(Dimethylamino)ethyl]-5-fluoro-2-methyl-1-[[4-(methylsulfide)phenyl]methylene]-1H-indene-3-acetamide | 1.47 |

| SRI # | Chemical Name | IC$_{50}$ (um) |
|---|---|---|
| 21387 | Ethanone, 2-[5-fluoro-2-methyl-1-[[4-(methylsulfonyl)phenyl]methylene]-1H-inden-3-yl]-1-(4-methylpiperazinyl) | 71 |
| 21540 | N-[[4-(Dimethylamino)phenyl]methyl]-(Z)-5-fluoro-2-methyl-3-[[4-(methylthio)phenyl]methylene]-1H-indene-3-acetamide | 3.222 |
| 21596 | N,2-Dimethyl-(Z)-5-fluoro-2-methyl-N-[2-(methylamino)ethyl]-3-[[4-(methylthio)phenyl]methylene]]-1H-indene-3-acetamide | 1.625 |
| 21590 | N-[[4-(Dimethylamino)phenyl]-(Z)-5-fluoro-2-methyl-3-[[4-(methylsulfinyl)phenyl]methylene]]-1H-indene-3-acetamide | 229.9 |
| 21487 | N-[2-(Dimethylamino)ethyl]-(Z)-5-fluoro-2-methyl-3-[[4-(methylsulfonyl)phenyl]methylene]]-1H-indene-3-acetamide | 10 |
| 21623 | N-[[4-(Dimethylamino)phenyl]-(Z)-5-fluoro-2-methyl-3-[[4-(methylthio)phenyl]methylene]]-1H-indene-3-acetamide | Not Active Below 100 uM |

In above tables-Growth inhibitory activity of sulindac and a group of SRI derivatives against the human HT29 colon tumor cell line. Activity is expressed as potency by the IC$_{50}$ value (50% inhibitory concentration). It is noted that 4-N,N dimethyl phenylamide compounds of this disclosure are not especially preferred since they are less active than the 4-N,N dimethyl benzylamide compounds. For instance, compare compound 21590 and 21623 to 21275 and 21540, respectively. Also, it is believed that the SCH$_3$ compound (21623) is less active than the corresponding SOCH$_3$ (21590) due at least in part to being less hydrophilic resulting in the noted solubility issues during the bioassay.

In keeping with the present disclosure, the derivatives of sulindac can be used alone or in appropriate association, and also may be used in combination with pharmaceutically acceptable carriers and other pharmaceutically active compounds such as various cancer treatment drugs including NSAIDs and/or along with radiation. The active agent may be present in the pharmaceutical composition in any suitable quantity. The pharmaceutical compositions can include components typically used for such purposes.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices. Another additive for the pharmaceutical compositions can be cyclodextrin for enhancing absorption of the active agent.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can include (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, such as sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The derivatives of sulindac alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, such as sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

The present disclosure further provides a method of treating precancerous conditions or dysplosia (i.e.—intraepithelial neoplasia) as well as cancer in a mammal, especially humans. The method comprises administering an effective treatment amount of a derivative of sulindac disclosed above to the mammal.

As regards these applications, the present method includes the administration to an animal, particularly a mammal, and more particularly a human, of a therapeutically effective amount of the compound effective in the inhibition of neoplasia and tumor growth and treating malignant disease including metastases, especially colorectal cancer. The method also includes the administration of a therapeutically effect amount of the compound for the treatment of and precancerous lesions such as adenomatous polyps of the colon and other dysplastic lesions of the skin (actinic keratosis), bladder, cervix, esophagus, oral cavity, lung, prostate and breast sometimes referred to as intraepithelial neoplasia.

The disclosed compounds and compositions can be administered to treat a number of cancers, including leukemias and lymphomas such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The present disclosure also relates to treating certain chronic inflammatory conditions which NSAIDs have shown benefit, but may be contraindicated due to cyclooxygenase inhibition (i.e.—inflammatory bowel disease) or do not appear to require cyclooxygenase inhibition for efficacy such as certain neurodegenerative diseases, including Alzheimer's Disease.

The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to affect the desired response. The preferred dosage is the amount which results in maximum inhibition of cancer, without unmanageable side effects.

The total amount of the compound of the present disclosure administered in a typical treatment is typically between about 10 mg/kg and about 1000 mg/kg of body weight for mice, and between about 100 mg/kg and about 500 mg/kg of body weight, and more typically between 200 mg/kg and about 400 mg/kg of body weight for humans per daily dose. This total amount is typically, but not necessarily, administered as a series of smaller doses over a period of about one time per day to about three times per day for about 24 months, and more typically over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

The method disclosed also comprises further administering a chemotherapeutic agent other than the derivatives of the present invention. Any suitable chemotherapeutic agent can be employed for this purpose. The chemotherapeutic agent is typically selected from the group consisting of alkylating agents, antimetabolites, natural products, anti-inflammatory agents, hormonal agents, molecular targeted drugs, anti-angiogenic drugs, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside fluorouracil, gemcitabine, mercaptopurine, methotrexate, thioguanine, floxuridine, fludarabine, and cladribine.

Examples of chemotherapeutic agents that are natural products include actinomycin D, bleomycin, camptothecins, daunomycin, doxorubicin, etoposide, mitomycin C, paclitaxel, taxoteredocetaxel, tenisposide, vincristine, vinblastine, vinorelbine, idarubicin, mitoxantrone, mithramycin and deoxycoformycin.

Examples of hormonal agents include antiestrogen receptor antagonists such as tamoxifen and fluvestrant, aromatase inhibitors such as anastrozole, androgen receptor antagonists such as cyproterone and flutamine, as well as gonadotropin release hormone agonists such as leuprolide. Examples of anti-inflammatory drugs include adrenocorticoids such as prednisone, and nonsteroidal anti-inflammatory drugs such as sulindac or celecoxib. Examples of molecular targeted drugs include monoclonal antibodies such as rituximab, cetuximab, trastuzumab and small molecules such as imatinib, erlotinib, ortizumib. Examples of anti-angiogenic drugs include thalidomide and bevacizimab. Examples of the aforesaid miscellaneous chemotherapeutic agents include mitotane, arsenic trioxide, tretinoin, thalidomide, levamisole, L-asparaginase and hydroxyurea.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference.

What is claimed is:

1. Compound selected from the group consisting of being N-[2-(dimethylamino)ethyl]-5-fluoro-2-methyl-1-[[4-(methylsulfinyl)phenyl]methylene]-1H-indene-3-acetamide, 5-fluoro-2-methyl-N-[(1-methyl-2-pyrrolidinyl)ethyl]-1-[[4-(methylsulfinyl)phenyl]methylene]-1H-indene-3-acetamide, 5-fluoro-2-methyl-1-[[4-(methylsulfinyl)phenyl]methylene]-N-[2-(1-piperazinyl)ethyl]-1H-indene-3-acetamide, 5-fluoro-2-methyl-1-[[4-(methylsulfinyl)phenyl]methylene]-N-[2-(1-piperidinyl)ethyl]-1H-indene-3-acetamide, 5-fluoro-2-methyl-1-[[4-(methylsulfinyl)phenyl]methylene]-N-[2-(3-pyridinyl)ethyl]-1H-indene-3-acetamide, 5-fluoro-2-methyl-1-[[4-(methylsulfinyl)phenyl]methylene]-N-[2-(4-morpholinyl)ethyl]-1H-indene-3-acetamide, 5-fluoro-2-methyl-1-[[4-(methylsulfinyl)phenyl]methylene]-N-[2-(1-pyrrolidinyl)ethyl]-1H-indene-3-acetamide, N,2-dimethyl-N-[2-(dimethylamino)ethyl]-5-fluoro-1-[[4-ethylsulfinyl)phenyl]methylene]-1H-indene-3-acetamide, N-(2-aminoethyl)-5-fluoro-2-methyl-1-[[4-(methylsulfinyl)phenyl]methylene]-1H-indene-3-acetamide, N-[2-(dimethylamino)ethyl]-5-fluoro-2-methyl-1-[[4-(methylthio)phenyl]methylene]-1H-indene-3-acetamide, 5-fluoro-2-methyl-1-[[4-(methylsulfinyl)phenyl]methylene]-N-(phenylmethyl)-1H-indene-3-acetamide, 5-fluoro-N-(2-furanylmethyl)-2-methyl-1-[[4-(methylsulfinyl)phenyl]methylene]-1H-indene-3-acetamide, 5-fluoro-N-[2-(4- imidnzolyl)ethyl]-2-methyl-1-[[4-(methylsulfinyl)phenyl] methylene-1H-indene-3-acetamide, 5-fluoro-N-[2-(N,N-diethylamino)ethyl]-2-methyl-1-[[4-(methylsulfinyl) phenyl]methylene-1H-indene-3-acetamide, N-[[4-(dimethylamino)phenyl]methyl]-5-fluoro-2-methyl-1-[[4-(methylsulfinyl)phenyl]methylene]-1H-indene-3-acetamide, ethanone, 2-[5-fluoro-2-methyl-1-[[4-(methylsulfinyl)phenyl]methylene]-1H-inden-3-yl]-1-(4-methylpiperazinyl), N-[[4-(dimethylamino)phenyl]methyl]-(Z)-5-fluoro-2-methyl-3-[[4-(methylthio)phenyl]methylene]-1H-indene-3-acetamide, N,2-dimethyl-(Z)-5-fluoro-2-methyl-N-[2-(methylamino)ethyl]-[[4-(methylthio)phenyl]methylene]]-1H-indene-3-acetamide, N-[[4-(dimethylamino)phenyl]-(Z)-5-fluoro-2-methyl-3-[[4-(methylsulfinyl)phenyl]methylene]]-1H-indene-3-acetamide, N-[2-(dimethylamino)ethyl]-(Z)-5-fluoro-2-methyl-3-[[4-(methylsulfonyl)phenyl]methylene]]-1H-indene-3-acetamide, and N-[2-(dimethylamino)ethyl]-5-fluoro-2-methyl-1-[[4-(methylsulfide)phenyl]methylene]-1H-indene-3-acetamide, and pharmaceutically acceptable salts thereof.

2. The compound of claim 1 being N-[2-(dimethylamino)ethyl]-5-fluoro-2-methyl-1-[[4-(methylsulfinyl)phenyl]methylene]-1H-indene-3-acetamide or pharmaceutically acceptable salts thereof.

3. The compound of claim 1 being fluoro-2-methyl-N-[(1-methyl-2-pyrrolidinyl)ethyl]-1-[[4-(methylsulfinyl)phenyl]methylene]-1H-indene-3-acetamide or pharmaceutically acceptable salt thereof.

4. The compound of claim 1 being 5-fluoro-2-methyl-1-[[4-(methylsulfinyl)phenyl]methylene]-N-[2-(1-piperazinyl)ethyl]-1H-indene-3-acetamide or pharmaceutically acceptable salt thereof.

5. The compound of claim 1 being 5-fluoro-2-methyl-1-[[4-(methylsulfinyl)phenyl]methylene]-N-[2-(1-piperidinyl)ethyl]-1H-indene-3-acetamide or pharmaceutically acceptable salt thereof.

6. The compound of claim 1 being 5-fluoro-2-methyl-[[4-(methylsulfinyl)phenyl]methylene]-N-[2-(1-pyridinyl) ethyl]-1H-indene-3-acetamide or pharmaceutically acceptable salt thereof.

7. The compound of claim 1 being 5-fluoro-2-methyl-[[4-(methylsulfinyl)phenyl]methylene]-N-[2-(4-morpholinyl) ethyl]-1H-indene-3-acetamide or pharmaceutically acceptable salt thereof.

8. The compound of claim 1 being 5-fluoro-2-methyl-1-[[4-(methylsulfinyl)phenyl]methylene]-N-[2-(1-pyrrolidinyl)ethyl]-1H-indene-3-acetamide or pharmaceutically acceptable salt thereof.

9. The compound of claim 1 being N,2-dimethyl-N-[2-(dimethylamino)ethyl]-5-fluoro-1-[[4-ethylsulfinyl)phenyl] methylene]-1H-indene-3-acetamide or pharmaceutically acceptable salt thereof.

10. The compound of claim 1 being N-(2-aminoethyl)-5-fluoro-2-methyl-1-[[4-(methylsulfinyl)phenyl]methylene]-1H-indene-3-acetamide or pharmaceutically acceptable salt thereof.

11. The compound of claim 1 being N-[2-(dimethylamino)ethyl]-5-fluoro-2-methyl-1-[[4-(methylthio)phenyl]methylene]-1H-indene-3-acetamide or pharmaceutically acceptable salt thereof.

12. The compound of claim 1 being 5-fluoro-2-methyl-1-[[4-(methylsulfinyl)phenyl]methylene]-N-(phenylmethyl)-1H-indene-3-acetamide or pharmaceutically acceptable salt thereof.

13. The compound of claim 1 being 5-fluoro-N-(2-furanylmethyl)-2-methyl-1-[[4-(methylsulfinyl)phenyl]methylene]-1H-indene-3-acetamide or pharmaceutically acceptable salt thereof.

14. The compound of claim 1 being 5-fluoro-N-[2-(4-imidazolyl)ethyl]-2-methyl-1-[[4-(methylsulfinyl)phenyl]methylene-1H-indene-3-acetamide or pharmaceutically acceptable salt thereof.

15. The compound of claim 1 being 5-fluoro-N-[2-(N,N-diethylamino)ethyl]-2-methyl-1-[[4-(methylsulfinyl)phenyl]methylene-1H-indene-3-acetamide or pharmaceutically acceptable salt thereof.

16. The compound of claim 1 being N-[[4-(dimethylamino)phenyl]methyl]-5-fluoro-2-methyl-1-[[4-(methylsulfinyl)phenyl]methylene]-1H-indene-3-acetamide or pharmaceutically acceptable salt thereof.

17. The compound of claim 1 being ethanone, 2-[5-fluoro-2-methyl-1-[[4-(methylsulfinyl)phenyl]methylene]-1H-inden-3-yl]-1-(4-methylpiperazinyl) or pharmaceutically acceptable salt thereof.

18. The compound of claim 1 being N-[[4-(dimethylamino)phenyl]methyl]-(Z)-5-fluoro-2-methyl-3-[[4-(methylthio)phenyl]methylene]-1H-indene-3-acetamide or pharmaceutically acceptable salt thereof.

19. The compound of claim 1 being N,2-dimethyl-(Z)-5-fluoro-2-methyl-N-[2-(methylamino)ethyl]-3-[[4-(methylthio)phenyl]methylene]-1H-indene-3-acetamide or pharmaceutically acceptable salt thereof.

20. The compound of claim 1 being N-[[4-(dimethylamino)phenyl]-(Z)-5-fluoro-2-methyl-3-[[4-(methylsulfinyl)phenyl]methylene]]-1H-indene-3-acetamide or pharmaceutically acceptable salt thereof.

21. The compound of claim 1 being N-[2-(dimethylamino)ethyl]-(Z)-5-fluoro-2-methyl-3-[[4-(methylsulfonyl)phenyl] methylene]]-1H-indene-3-acetamide or pharmaceutically acceptable salt thereof.

22. The compound of claim 1 being N-[2-(dimethylamino)ethyl]-5-fluoro-2-methyl-1-[[4-(methylsulfide)phenyl]methylene]-1H-indene-3-acetamide or the pharmaceutically acceptable salt thereof.

23. A pharmaceutical composition comprising at least one compound according to claim 1 and a pharmaceutically acceptable carrier.

24. A method of treating a cancer in a mammal comprising administering to the mammal an effective treatment amount of at least one compound according to claim 1 or a pharmaceutically acceptable salt thereof; wherein the cancer is selected from the group consisting of colon, lung, ovarian, lymphoma, prostate, colon, breast, myeloma, melanoma, pancreatic, liver and leukemia.

25. The method of claim 24, wherein the cancer is colon cancer.

26. The method of claim 24 wherein the treatment amount is from about 10 mg/kg to about 1000 mg/kg of the body weight of the mammal.

27. The method of claim 24 wherein the treatment amount is from about 100 mg/kg to about 500 mg/kg of the body weight of the mammal.

28. The method of claim 24 wherein the treatment is carried out over a period of from one time per day to about 3 times per day for 24 months.

29. The method of claim 24 wherein the derivative is administered orally, intravenously or intraperitoneally.

30. The method of claim 25 wherein the mammal is human.

31. A method for preparing a compound according to claim 1 which comprises reacting sulindac with a compound represented by the formula: $NH_2(CH_2)_m NR_1 R_2$.

32. A method of treating cancer in a mammal comprising administering to the mammal an effective treatment amount of at least one compound according to claim 11 or a pharmaceutically acceptable salt thereof; wherein the cancer is selected from the group consisting of colon, lung, ovarian, lymphoma, prostate, colon, breast, myeloma, melanoma, pancreatic, liver and leukemia.

33. A method of treating colon cancer in a mammal comprising administering to the mammal an effective treatment amount of the compound according to claim 11 or a pharmaceutically acceptable salt thereof.

* * * * *